(12) United States Patent
Zhang et al.

(10) Patent No.: US 11,866,737 B2
(45) Date of Patent: Jan. 9, 2024

(54) 2-ISOPROPYLMALATE SYNTHETASE AND ENGINEERING BACTERIA AND APPLICATION THEREOF

(71) Applicant: Tianjin University of Science and Technology, Tianjin (CN)

(72) Inventors: Chenglin Zhang, Tianjin (CN); Qingyang Xu, Tianjin (CN); Yanjun Li, Tianjin (CN); Yu Zhang, Tianjin (CN); Yingzi Li, Tianjin (CN); Fuzhou Zhu, Tianjin (CN); Nan Lu, Tianjin (CN); Shibao Han, Tianjin (CN); Xierong Dong, Tianjin (CN); Zishen Wang, Tianjin (CN); Hao Xu, Tianjin (CN); Ziyi Li, Tianjin (CN)

(73) Assignee: Tianjin University of Science and Technology, Tianjin (CN)

( * ) Notice: Subject to any disclaimer, the term of this patent is extended or adjusted under 35 U.S.C. 154(b) by 199 days.

(21) Appl. No.: 17/137,327

(22) Filed: Dec. 29, 2020

(65) Prior Publication Data

US 2021/0189354 A1    Jun. 24, 2021

Related U.S. Application Data

(63) Continuation of application No. PCT/CN2020/112038, filed on Aug. 28, 2020.

(51) Int. Cl.
*C12N 9/10* (2006.01)
*C12P 13/06* (2006.01)

(52) U.S. Cl.
CPC ............ *C12N 9/1025* (2013.01); *C12P 13/06* (2013.01); *C12Y 203/03013* (2013.01)

(58) Field of Classification Search
CPC ....... C12N 9/1025; C12N 15/52; C12P 13/06; C12Y 203/03013; C12Y 101/01085; C12Y 202/01006; C12Y 402/01033
See application file for complete search history.

(56) References Cited

FOREIGN PATENT DOCUMENTS

| CN | 1280135 A | 1/2001 |
|---|---|---|
| CN | 104302765 A | 1/2015 |
| CN | 104480058 A | 4/2015 |
| CN | 104531598 A | 4/2015 |
| CN | 105886431 A | 8/2016 |
| CN | 106754807 A | 5/2017 |
| CN | 108884449 A | 11/2018 |
| CN | 109294966 A | 2/2019 |
| CN | 110229797 A | 9/2019 |
| EP | 1108790 A2 | 6/2001 |
| EP | 1568776 A2 | 8/2005 |
| WO | 2008088104 A | 7/2008 |

*Primary Examiner* — Iqbal H Chowdhury

(57) ABSTRACT

The invention relates to a 2-isopropyl malate synhase, a genetically engineered bacterium for producing L-leucine and application thereof and belongs to the field of metabolic engineering. The genetically engineered bacterium is obtained by overexpressing an isopropyl malate synthase coding gene leuA$^M$ for relieving feedback inhibition by L-leucine, an acetohydroxy acid synthase coding gene ilvBN$^M$ for relieving feedback inhibition by L-isoleucine, a 3-isopropyl malate dehydrogenase coding gene leuB and a 3-isopropyl malate dehydratase coding gene leuCD in host cells. The genetically engineered bacterium for producing the L-leucine is free from nutritional deficiency, rapid in growth, short in fermentation period, high in yield and high in conversion rate.

11 Claims, 3 Drawing Sheets

Specification includes a Sequence Listing.

2-ISOPROPYLMALATE SYNTHETASE AND ENGINEERING BACTERIA AND APPLICATION THEREOF

REFERENCE TO AN ELECTRONIC SEQUENCE LISTING

The contents of the electronic sequence listing (SEQUENCE-LISTING-20200709-DTJKJUSN.txt; Size: 33,000 bytes; and Date of Creation: Mar. 14, 2021) is herein incorporated by reference in its entirety.

CROSS REFERENCE TO RELATED APPLICATION

The application claims priority to Chinese Patent Application No. CN201910820591X, filed on Aug. 29, 2019, and entitled "Isopropyl Malate Synthase and Application thereof", and Chinese Patent Application No. CN2019108860780, filed on Sep. 19, 2019, and entitled "Genetically Engineered Bacterium for Producing L-leucine and Application thereof", the entire contents of which are incorporated herein by reference.

TECHNICAL FIELD

The invention relates to a 2-isopropyl malate synthase, a genetically engineered bacterium for producing L-leucine and application thereof and belongs to the field of metabolic engineering.

BACKGROUND ART

L-leucine belongs to branched chain amino acids and is one of the eight amino acids essential to human body and a raw material for synthesizing proteins and hormones, playing a vital role in the life activities of human body. Therefore, the L-leucine has a very broad marketing and application prospect in the industries such as food and medicine.

Industrial methods for synthesizing L-leucine include a hair extraction method and a fermentation method, wherein the hair extraction method, however, has the shortcomings of limited raw material resources, high production costs, environmental pollution and the like. Accordingly, the fermentation method is the mainstream method for producing the L-leucine. Existing industrial production strains of the L-leucine are mainly obtained through mutagenesis and have the shortcomings of nutritional deficiency, slow growth, unstable hereditary characters, causing the problems long fermentation period, unstable fermentation performance, low yield and conversion rate, and the like.

SUMMARY OF THE INVENTION

The present disclosure provides an isopropyl malate synthase for relieving the feedback inhibition by the L-leucine and a coding gene thereof, and constructs a genetically engineered bacterium for producing the L-leucine by the coding gene. The present disclosure overcome the shortcomings that existing wild type isopropyl malate synthases are subjected to feedback inhibition by the L-leucine and existing L-leucine production strains are slow in growth, deficient in nutrition, unstable in fermentation and the like.

One of the technical solutions of the present invention is to provide an isopropyl malate synthase mutant LEUA$^M$ for relieving the feedback inhibition by the L-leucine, of which the amino acid sequence is shown as SEQ ID NO. 1, and the coding gene of the isopropyl malate synthase mutant is leuA$^M$, of which the nucleotide sequence is shown as SEQ ID NO. 2.

The isopropyl malate synthase mutant originates from a Corynebacterium glutamicum mutant strain, of which the artificial mutation process comprises taking Corynebacterium glutamicum ATCC13032 as an original strain, performing plasma mutagenesis at atmospheric pressure and room temperature, and screening out a strain LEU262 on a minimal medium containing 50 mg/L leucine hydroxamate; then taking the strain LEU262 as an original strain, performing plasma mutagenesis at atmospheric pressure and room temperature, and screening out a strain LEU741 on a minimal medium containing 50 mg/L beta-hydroxyleucine.

The genome of the strain LEU741 is extracted, primers are designed for performing PCR (polymerase chain reaction) amplification of the 2-isopropyl malate synthase coding gene, and PCR products are recovered and sequenced; the 2-isopropyl malate synthase encoded by the gene is discovered to have the following amino acid mutations compared with the wild type 2-isopropyl malate synthase from the Corynebacterium glutamicum ATCC13032: F7L, I14F, I51S, G127D, I197V, F370L, K380M, R529H, G561D and V596A.

The Present Invention Adopts the Following Definitions

1. Identification of the Isopropyl Malate Synthase Mutant

'original amino acid+position+amino acid after substituted' is used to represent the mutated amino acids in the 2-isopropyl malate synthase mutant. For example, F7L represents that the amino acid at the position 7 is Leu substituted from Phe in the wild type 2-isopropyl malate synthase, F7 represents that the amino acid at the position 7 is Phe, and the number of the position corresponds to that in the amino acid sequence of the wild type 2-isopropyl malate synthase in SEQ ID No. 3.

According to the present invention, leuA represents a wild type 2-isopropyl malate synthase coding gene (as shown in SEQ ID NO. 4), LEUA represents a wild type 2-isopropyl malate synthase (as shown in SEQ ID NO. 3), leuA$^M$ represents a mutated 2-isopropyl malate synthase gene (as shown in SEQ ID NO. 2), and LEUA$^M$ represents the 2-isopropyl malate synthase mutant (as shown in SEQ ID NO. 1). Comparison of the amino acids before and after the mutation is as follows:

| 2-isopropyl malate synthase | Amino acids |
|---|---|
| LEUA | F7, I14, I51, G127, I197, F370, K380, R529, G561, V596 |
| LEUA$^M$ | F7L, I14F, I51S, G127D, I197V, F370L, K380M, R529H, G561D, V596A |

The 2-isopropyl malate synthase mutant LEUA$^M$ has the following enzymatic characteristics that, under the condition that the concentration of L-leucine ranges from 0-15 mmol/L, the enzymatic activity of the LEUA$^M$ has no significant change, which means that the mutant of the present invention relieves the feedback inhibition of the L-leucine. Meanwhile, the enzymatic activity of the LEUA$^M$ under the condition that the concentration of L-leucine ranges from 0-15 mmol/L has no significant decrease compared with that of the wild type 2-isopropyl malate synthase LEUA under the condition that the concentration of L-leucine is 0-mmol/L.

Another technical solution of the present invention to the problem is to provide a genetically engineered bacterium for producing L-leucine, wherein the genetically engineered bacterium is obtained by overexpressing the isopropyl malate synthase coding gene leuA$^M$ for relieving the feedback inhibition of the L-leucine, an acetohydroxy acid synthase coding gene ilvBN$^M$ for relieving the feedback inhibition of L-isoleucine, a 3-isopropyl malate dehydrogenase coding gene leuB and a 3-isopropyl malate dehydratase coding gene leuCD in host cells.

The host cells can be *Escherichia coli*, *Corynebacterium glutamicum*, *Bacillus subtilis*, *Bacillus megaterium*, *Bacillus amyloliquefaciens*, *Vibrio natriegens*, *Saccharomyces cerevisiae* and the like.

An acetohydroxy acid synthase encoded by the gene ilvBN$^M$ in the present disclosure relieves the feedback inhibition of the L-isoleucine, and the nucleotide sequence of the gene ilvBN$^M$ is shown as SEQ ID NO. 5.

The gene leuB in the present disclosure can be obtained from *Escherichia coli*, *Corynebacterium glutamicum*, *Bacillus subtilis*, *Bacillus megaterium* and the like, such as those with Genbank accession numbers of b0073, JW5807, NCgl1237, BSU28270 and BAMF_2634.

The gene leuCD in the present disclosure can be obtained from *Escherichia coli*, *Corynebacterium glutamicum*, *Bacillus subtilis*, *Bacillus megaterium* or the like, such as those with Genbank accession numbers of b0071, b0072, JW0070, JW0071, NCgl1262, NCgl1263, BSU28250, BSU28260, BAMF_2632 and BAMF_2633.

In the preferred embodiments, the genetically engineered bacterium in the present disclosure is obtained by taking *Escherichia coli* W3110 as the host cells to overexpress the gene leuA$^M$ as shown in SEQ ID NO. 2, the gene ilvBN$^M$ as shown in SEQ ID NO. 5 and the gene leuBCD (an operon composed of the leuB and the leuCD in *Escherichia coli*) as shown in SEQ ID NO.6. The preferred genetically engineered bacterium in the present disclosure producing the L-leucine is strain TE03.

Further, the construction method of the genetically engineered bacterium is as follows:
(4) performing amplification of the isopropyl malate synthase coding gene leuA$^M$ and the acetohydroxy acid synthase coding gene ilvBN$^M$ separately, and constructing genome integration fragments separately;
(5) performing amplification of the gene leuBCD, and connecting it with a plasmid to obtain a recombinant plasmid;
(6) performing expression of the genome integration fragments and the recombinant plasmid in previous steps subsequently in the host cells by the CRISPR/Cas9 gene editing technology.

Further, the construction method of the genetically engineered bacterium specifically comprises:
(5) taking the genome of *Escherichia coli* W3110 as a template to perform PCR amplification to obtain the isopropyl malate synthase coding gene leuA$^M$ and UHF and DHF fragments (respectively the upstream homologous arm and the downstream homologous arm of gene lacI), and then performing overlapping PCR to obtain a recombinant fragment UHF-leuA$^M$-DHF;
The nucleotide sequence of the UHF is shown as SEQ ID NO. 7;
The nucleotide sequence of the DHF is shown as SEQ ID NO. 8;
(6) obtaining UHFA and DHFB fragments (respectively the upstream homologous arm and the downstream homologous arm of gene lacZ) and ilvBN$^M$ gene segment by the same principle of previous step, and performing overlapping PCR on those fragments to obtain a recombinant fragment UHF-ilvBN$^M$-DHF;
The nucleotide sequence of the UHFA is shown as SEQ ID NO. 9;
The nucleotide sequence of the DHFB is shown as SEQ ID NO. 10;
(7) taking the genome of the *Escherichia coli* W3110 as a template to perform PCR amplification to obtain the gene leuBCD, and connecting the gene leuBCD with a plasmid pTrc99a to obtain a recombinant plasmid pTR-leuBCD;
(8) performing construction of the L-leucine genetically engineered bacterium TE03; annealing PG-1 and PG-2 as well as PG-3 and PG-4 respectively at 52° C. and then connecting PG-1 and PG-2 as well as PG-3 and PG-4 to a plasmid pGRB to obtain pGRB1 and pGRB2; taking *Escherichia coli* W3110 as an original strain, and performing transformation of pGRB1 and UHF-leuA$^M$-DHF respectively into the *Escherichia coli* W3110 to obtain a recombinant strain TE01; taking the strain TE01 as an original strain and performing transformation of pGRB2 and UHFA-ilvBN$^M$-DHFB respectively into TE01 to obtain a strain TE02; and then performing transformation of pTR-leuBCD into strain TE02 to obtain strain TE03.

The invention also provides a method for synthesizing L-leucine with the genetically engineered bacterium through fermentation. The method specifically includes:
inoculating a seed culture at an inoculum size of 5-10% onto a fermentation culture medium for fermentation culture, wherein the content of dissolved oxygen is maintained at 20-40%, the pH is maintained at 6.5-7.5, the culture temperature is 30-35° C., the fermentation period is 40-48 h, and the residual sugar concentration is maintained at 0-0.4% (W/V) during the fermentation.

At the end of the fermentation, the concentration of the L-leucine in the fermentation liquid reaches 60.5-69.6 g/L.

The fermentation culture medium is composed of 25 g/L glucose, 12 g/L peptone, 4 g/L yeast powder, 3.5 g/L KH$_2$PO$_4$, 1.5 g/L MgSO$_4$, 15 mg/L FeSO$_4$, 15 mg/L MnSO$_4$ and 0.01 mg/L VB1 (vitamin B1). The pH of the fermentation culture medium is 7.0, the pressure is 0.075 MPa, and the fermentation culture medium is subjected to high-pressure steam sterilization for 15 min.

The present disclosure possesses the following advantages:
1. The 2-isopropyl malate synthase encoded by the gene leuA$^M$ of the present disclosure has the characteristics that the 2-isopropyl malate synthase relieves the feedback inhibition effects of L-leucine (as shown in FIG. 1). Under the condition that the concentration of L-leucine ranges from 0-15 mmol/L, the enzymatic activity of the LEUA$^M$ has no significant change and meanwhile has no significant decrease compared with that of the wild type 2-isopropyl malate synthase encoded by the gene leuA (as shown in FIG. 2).
2. The L-leucine genetically engineered bacterium strain TE03 has the advantages of no nutritional deficiency, rapid growth, short fermentation period, high yield and high conversion rate. After 40-48 h of fermentation by the strain TE03, the concentration of L-leucine in the fermentation liquid reaches 60.5-69.6 g/L (as shown in FIG. 3).

DETAILED DESCRIPTION OF THE INVENTION

Figure 1:
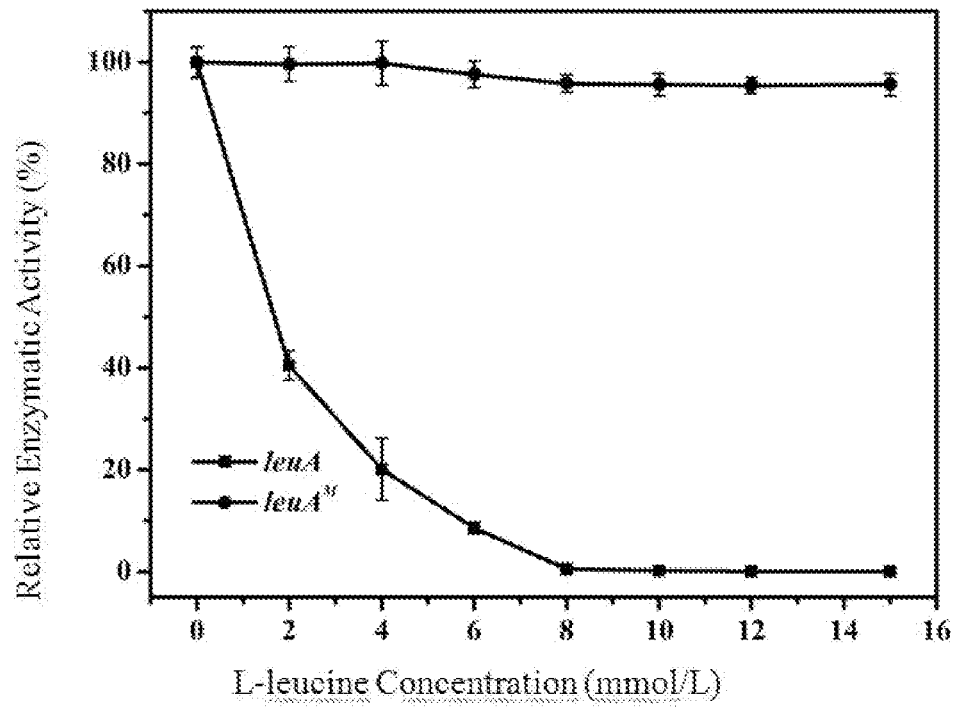
FIG. 1: Influence of L-leucine on the activity of the 2-isopropyl malate synthase encoded by the genes leuA and leuA$^M$.

In order to make the objects, technical solutions and advantages of the present invention clearer and more apparent, the present invention is further described in detail with reference to the following embodiments. It should be understood that the embodiments described herein are only intended to illustrate of the present invention but not to limit the present invention.

The present embodiment provides a genetically engineered bacterium for producing L-leucine, which is constructed by overexpressing an isopropyl malate synthase coding gene leuA$^M$ for relieving the feedback inhibition by L-leucine, an acetohydroxy acid synthase coding gene ilvBN$^M$ for relieving the feedback inhibition by L-isoleucine, a 3-isopropyl malate dehydrogenase coding gene leuB and a 3-isopropyl malate dehydratase coding gene leuCD in host cells.

In some embodiments, the host cells can be *Escherichia coli*, *Corynebacterium glutamicum*, *Bacillus subtilis*, *Bacillus megaterium*, *Bacillus amyloliquefaciens*, *Vibrio natriegens*, *Saccharomyces cerevisiae* and the like.

In some embodiments, the gene ilvB1Vm is derived from *Corynebacterium glutamicum* which is resistant to such L-isoleucine-structured analogues as α-aminobutyric acid and thioisoleucine.

In some embodiments, the gene leuB is selected from those with Genbank accession numbers of b0073, JW5807, NCg11237, BSU28270 or BAMF_2634.

In some embodiments, the gene leuCD is selected from those with Genbank accession numbers of b0071, b0072, JW0070, JW0071, NCg11262, NCg11263, BSU28250, BSU28260, BAMF_2632 or BAMF_2633.

The host cells, the gene ilvBN$^M$, the gene leuB and the gene leuCD from the above sources can all achieve the effects of the present invention. In the following embodiments, *Escherichia coli* W3110 is taken as the host cells to overexpress the gene leuA$^M$ shown in SEQ ID NO. 2, the gene ilvBN$^M$ shown in SEQ ID NO. 5 and leuBCD (an operon composed of the leuB and the leuCD in the *Escherichia coli*) shown in SEQ ID NO. 6 to construct the genetically engineered bacterium strain TE03 for producing L-leucine to illustrate the present invention in an exemplary manner.

Sequence table of primers applied in the following embodiments:

| Names | Sequences | SEQ ID NO. |
|---|---|---|
| LEUA-1 | GTGAAACCAGTAACGTTATACG | 11 |
| LEUA-2 | CCACACATTATACGAGCCGGATGATTAATTGTCAACCGTCTTCATGGGAGAA | 12 |
| LEUA-3 | CCGGCTCGTATAATGTGTGGAATTGTGAGCGGATAACAATTTCACACAAGGAGATATACATGTCTCCTAACGATGCATT | 13 |
| LEUA-4 | CAAACAACAGATAAAACGAAAGGCCCAGTCTTTCGACTGAGCCTTTCGTTTTATTTGCTTAAACGCCGCCAGC | 14 |
| LEUA-5 | TTCGTTTTATCTGTTGTTTGTCGGTGAACGCTCTCCTGAGTAGGACAAATGCTGTTAGCGGGC | 15 |
| LEUA-6 | TCACTGCCCGCTTTCCAG | 16 |
| leuA-1' | ATGTCTCCTAACGATGCATT | 17 |
| leuA-2' | TTAAACGCCGCCAGC | 18 |
| IlvB-1 | ATGACCATGATTACGGATTCAC | 19 |
| IlvB-2 | CCACACATTATACGAGCCGGATGATTAATTGTCAACGGGTTTTCGACGTTCAGACGTA | 20 |
| IlvB-3 | CCGGCTCGTATAATGTGTGGAATTGTGAGCGGATAACAATTTCACACAAGGAGATATACCATGAATGTGGCAGCTTCTC | 21 |
| IlvB-4 | CAAACAACAGATAAAACGAAAGGCCCAGTCTTTCGACTGAGCCTTTCGTTTTATTTGTTAGATCTTGGCCGGAGCCATGGTC | 22 |
| IlvB-5 | GACTGGGCCTTTCGTTTTATCTGTTGTTTGTCGGTGAACGCTCTCCTGAGTAGGACAAATTTGATGGTAGTGGTCAAATGG | 23 |
| IlvB-6 | TTATTTTTGACACCAGACCAA | 24 |
| LA-1 | ATCATCACAGCAGCGGCCTGGTGCCGCGCATGTCTCCTAACGATGCATT | 25 |
| LA-2 | TGATGATGTTAGCTAGCGCTGAATTCTGCTTAAACGCCGCCAGC | 26 |
| leuBCD-1 | GACCATGGAATTCGAGCTCGGTACCCGGATGTCGAAGAATTACCATATTGCC | 27 |
| leuBCD-2 | CTTGCATGCCTGCAGGTCGACTCTAGAATAATTCATAAACGCAGGTTGTTTTG | 28 |
| PG-1 | AGTCCTAGGTATAATACTAGTTTCTCCCATGAAGACGGGTTTTAGAGCTAGAA | 29 |
| PG-2 | TTCTAGCTCTAAAACCCGTCTTCATGGGAGAAACTAGTATTATACCTAGGACT | 30 |
| PG-3 | AGTCCTAGGTATAATACTAGTAAACTGTGGAGCGCCGAAATCCGTTTTAGAGCTAGAA | 31 |
| PG-4 | TTCTAGCTCTAAAACGGATTTCGGCGCTCCACAGTTTACTAGTATTATACCTAGGACT | 32 |
| IV-1 | ATCATCACAGCAGCGGCCTGGTGCCGCGCATGACCATGATTACGGATTCAC | 33 |

-continued

| Names | Sequences | SEQ ID NO. |
|---|---|---|
| IV-2 | TGATGATGTTAGCTAGCGCTGAATTCTGCTTAGATCTTGGCCGGAGCCATGG | 34 |
| ilvBN-1 | ATGACCATGATTACGGATTCAC | 35 |
| ilvBN-2 | TTAGATCTTGGCCGGAGCCATGG | 36 |

Embodiment 1: Acquisition of the Isopropyl Malate Synthase Coding Gene leuA$^M$ for Relieving the Feedback Inhibition by L-Leucine (4) Screening of Mutant Strains Resistant to Structural Analogues of L-Leucine 1.1 Preparation of a Suspension of a *Corynebacterium glutamicum* ATCC13032

The *Corynebacterium glutamicum* ATCC13032 is inoculated into an LB (Luria broth) liquid medium for culture at 32 DEG C and 200 rpm for 12 h, centrifugation is performed for collecting bacterial cells, which are then washed with sterile normal saline for 3 times and then resuspended until $OD_{600}$ is 0.6-0.8, and 10 uL of the suspension is applied onto a slide glass.

1.2 Plasma Mutagenesis at Room Pressure and Temperature

Applied mutagenesis parameters include that the slide is arranged 2 mm away from an air flow port, the power is 120 W, the air flow velocity is 10 SLM (standard liter per minute), and the action period is 20 s.

1.3 Screening of the Mutant Strains Resistant to the L-Leucine-Structured Analogue-α-Aminobutyric Acid The suspension subjected to mutagenesis in the step 1.2 is spread onto a minimal medium containing 50 mg/L leucine hydroxamate for culture at 35 DEG C for 48 h, and then the strains with a large bacterial colony are selected.

1.4 Determination of L-Leucine Producing Capacity of the Strains

The strains screened in the step 1.3 are subjected to 96-well plate culture through a seed culture medium and then inoculated at an inoculum size of 5% into a 96-well plate containing a fermentation culture medium for a fermentation experiment, according to which the strain LEU262 is the highest in the yield of L-leucine.

1.5 Screening of the Mutant Strains Resistant to the L-Leucine-Structured Analogue-Thioisoleucine and Determination of L-Leucine Producing Capacity of the Strains The LEU262 is taken as a mutagenesis object. The steps 1.1 and 1.2 are repeated. The mutagenized suspension is applied onto a minimal medium containing 50 mg/L (3-hydroxy leucine for culture at 35 DEG C for 48 hours, then the strains with a large bacterial colony are selected, and the step 4) is repeated to determine that the strain LEU741 is the highest in the yield of L-leucine.

1.6 Culture Mediums

The seed culture medium is composed of 20 g/L glucose, 5 g/L yeast powder, 4 g/L $(NH_4)_2SO_4$, 2.5 g/L $KH_2PO_4$, 0.5 g/L $MnSO_4$ and 30 mL/L corn steep liquor, the pH is 6.5-7.0, and the seed culture medium is subjected to high-pressure steam sterilization at 115 DEG C for 15 min.

The fermentation culture medium is composed of 70 g/L glucose, 4 g/L $(NH_4)_2SO_4$, 1 g/L $KH_2PO_4$, 0.6 g/L $MgSO_4.7H_2O$, 0.02 g/L $MnSO_4$, 0.002 g/L VB1 and 30 mL/L corn steep liquor, the pH is 6.5-7.0, and the fermentation culture medium is subjected to high-pressure steam sterilization at 115 DEG C for 15 min.

1.7 Determination Method 8000 g of the fermentation liquor is centrifuged for 5 min, then the supernatant is extracted and subjected to derivatization reaction with 0.8% (V/V) 2,4-dinitrofluorobenzene, and the content of L-leucine is detected by high performance liquid chromatography under the conditions that Agilent C18 (15 mm*4.6 mm, 5 mum) is subjected to acetonitrile/sodium acetate binary gradient elution, the column temperature is 33 DEG C and the detection wavelength is 360 nm. According to the detection result of the high performance liquid chromatography and comparison with the peak appearance time and the peak area of a standard product, the yield of L-leucine can be determined.

(5) Acquisition of the Mutant of the Isopropyl Malate Synthase Coding Gene leuA$^M$ for Relieving the Feedback Inhibition of L-Leucine The genome of the strain LEU741 is extracted, primers leuA-1' and leuA-2' are applied to perform PCR amplification under the conditions: 94 DEG C, 5 min, 1 cycle; 94 DEG C, 30 s, 50 DEG C, 30 s, 72 DEG C, 2 min, 30 cycles; 72 DEG C,10 min,1 cycle. The volume of the reaction system is 100 uL. 10 uL of the PCR products is detected through 1.5% agarose gel electrophoresis. A target fragment amplified by PCR is recovered and connected to a pMD™18-T Vector and is then transformed into *Escherichia coli* (*E. coli* DH5a) competent cells, the cells are applied onto an LB solid culture medium containing ampicillin (100 ug/mL) for inverted culture at 37 DEG C for 24 h. 3 single colonies are picked, and recombinant plasmids are extracted and sequenced.

Sequencing results show that, compared with the wild type leuA, the 2-isopropyl malate synthase encoded by the mutated gene has mutations of F7L, I14F, I51S, G127D, I197V, F370L, K380M, R529H, G561D and V596A, the mutant is named as LEUA$^M$, and the coding gene is named as leuA$^M$ (6) Comparison of the Enzymatic Characteristics of the Isopropyl Malate Synthase Mutant LEUA$^M$ and the Wild Type Isopropyl Malate Synthase LEUA The genomes of the *Corynebacterium glutamicum* ATCC13032 and the strain LEU741 are taken as templates respectively, primers LA-1 and LA-2 are applied to perform PCR amplification. The products are recovered and connected to pET-His plasmids digested by BamH I and are then transformed into *Escherichia coli* BL21 (DE3) to obtain strains *E. coli*-leuA and *E. coli*-leuA$^M$, which are induced by IPTG (isopropyl-beta-thiogalactoside) to express recombinant proteins LEUA and LEUA$^M$, bacteria are collected, resuspended in 50 mmol/L Tris-HCl buffer solution (pH=7.5), subjected to ultrasonic disruption and centrifuged, and then the supernatant is collected.

Figure 2:
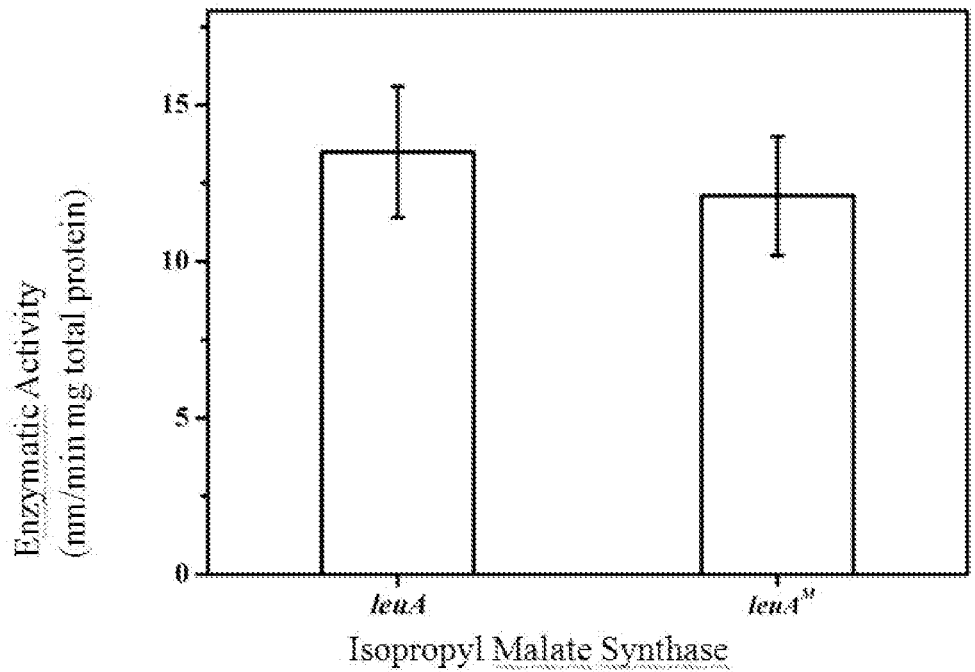
FIG. 2: Comparison of the activity of the 2-isopropyl malate synthases encoded by leuA$^M$ and leuA.

The enzymatic activities of the LEUA$^M$ and the LEUA are determined by the following method:

adding 10 uL of the above-described supernatant into 990 uL of Tris-HCl buffer solution (50 mmol/L, pH=7.5 and composed of 400 mmol/L potassium glutamate, 20 uL of 5, 5'-dithiobis (2-nitrobenzoic acid), 3 mmol/L acetyl-CoA and 4 mmol/L ketoisovaleric acid) for reaction at 30 DEG C for 1 h, and then adding 100 uL of sulfuric acid (3 mol/L) for treatment at 65 DEG C for 15 min to terminate the reaction, wherein, during the reaction, the 2-isopropyl malate synthase can catalyze the acetyl-CoA to produce coenzyme A, which has the maximum absorbance at $OD_{412}$. Therefore, according to the principle, the change value per minute of $OD_{412}$ can be measured through spectrophotometry to calculate the production of the coenzyme A and accordingly calculate the enzymatic activity. As results shown in FIG. 2, the activities of the $LEUA^M$ and the LEUA are 12.1 and 13.5 nmol/(min*mg*total protein), respectively, presenting no significant difference between them.

The influence of the L-leucine on the enzymatic activity of $LEUA^M$ and LEUA is determined by the following method:

0, 2, 4, 6, 8, 10, 12 and 15 mmol/L of L-leucine are respectively added into the above reaction solution, and then the amount of the produced coenzyme A is measured to study the performance of the $LEUA^M$ on relieving the feedback inhibition by the L-leucine. The enzymatic activity when the addition concentration of the L-leucine is 0 is defined as 100%. Compared with which the enzymatic activity of the $LEUA^M$ or the LEUA under other L-leucine concentration conditions is the relative enzymatic activity. As shown in FIG. 1, the relative activity of the LEUA decreases rapidly with increasing L-leucine concentration, and almost decreases to 0 when the L-leucine concentration is higher than 6 mmol/L. This indicates that the LEUA is subjected to the feedback inhibition by the L-leucine. While the relative enzymatic activity of the mutant $LEUA^M$ has no significant change with increasing L-leucine concentration, indicating that the $LEUA^M$ can relieve the feedback inhibition by the L-leucine.

It can be seen from the above results, the 2-isopropyl malate synthase mutant $LEUA^M$ relieves the feedback inhibition by the L-leucine and has no significant decrease in the activity compared with the wild type LEUA.

Embodiment 2: Acquisition of the Acetohydroxy Acid Synthase Coding Gene $ilvBN^M$ for Relieving the Feedback Inhibition by L-Isoleucine (4) Screening of Mutant Strains Resistant to L-Isoleucine-Structured Analogues 1.1 Preparation of a Suspension of a *Corynebacterium glutamicum* ATCC13032

The *Corynebacterium glutamicum* ATCC13032 is inoculated into an LB (Luria-Bertani) liquid medium for culture at 32 DEG C and 200 rpm for 12 h, centrifugation is performed for collecting bacterial cells, which are then washed with sterile normal saline for 3 times and then resuspended until $OD_{600}$ is 0.6-0.8, and 10 uL of the suspension is applied onto a slide.

1.2 Plasma Mutagenesis at Room Pressure and Temperature

Applied mutagenesis parameters include that the slide is arranged 2 mm away from an air flow port, the power is 120 W, the air flow velocity is 10 SLM, and the action period is 25 s.

1.3 Screening of the Mutant Strains Resistant to the L-Isoleucine-Structured Analogue of α-Aminobutyric Acid The suspension subjected to mutagenesis in the step 1.2 is applied onto a minimal medium containing 50 mg/L α-aminobutyric acid for culture at 35 DEG C for 48 h, and then the strains with a large bacterial colony are selected.

1.5 Determination of L-Isoleucine Producing Capacity of the Strains

The strains screened in the step 1.3 are subjected to 96-well plate culture through a seed culture medium and then inoculated at an inoculum size of 10% into a 96-well plate containing a fermentation culture medium for a fermentation experiment, according to which the strain ILE396 is the highest in the yield of L-isoleucine.

1.5 Screening of the Mutant Strains Resistant to the L-Isoleucine-Structured Analogue of Thioisoleucine and Determination of L-Leucine Producing Capacity of the Strains The ILE396 is taken as a mutagenesis object, the steps 1.1 and 1.2 are repeated, the mutagenized suspension is applied onto a minimal medium containing 50 mg/L thioisoleucine for culture at 35 DEG C for 48 hours, then the strains with a large bacterial colony are selected, and the step 4) is repeated to determine that the strain ILE693 is the highest in the yield of L-isoleucine.

1.6 Culture Mediums

The seed culture medium is composed of 25 g/L glucose, 5 g/L yeast powder, 5 g/L $(NH_4)_2SO_4$, 2 g/L $KH_2PO_4$, 0.6 g/L $MnSO_4$ and 40 mL/L corn steep liquor, the pH is 6.8-7.2, and the seed culture medium is subjected to high-pressure steam sterilization at 115 DEG C for 15 min.

The fermentation culture medium is composed of 80 g/L glucose, 3 g/L (NH4)2SO4, 1.5 g/L $KH_2PO_4$, 0.6 g/L $MgSO_4·7H_2O$, 0.015 g/L $MnSO_4$, 0.001 g/L VB1 and 30 mL/L corn steep liquor, the pH is 6.8-7.2, and the fermentation culture medium is subjected to high-pressure steam sterilization at 115 DEG C for 15 min.

1.7 Determination Method 8000 g of the fermentation liquor is centrifuged for 5 min, then the supernatant is extracted and subjected to derivatization reaction with 0.8% (V/V) 2, 4-dinitrofluorobenzene, and the content of L-isoleucine is detected by high performance liquid chromatography under the conditions that Agilent C18 (15 mm*4.6 mm, 5 mum) is subjected to acetonitrile/sodium acetate binary gradient elution, the column temperature is 33 DEG C and the detection wavelength is 360 nm. According to the detection result of the high performance liquid chromatography and comparison with the peak appearance time and the peak area of a standard product, the yield of L-isoleucine can be determined.

(5) Acquisition of the Mutant of the Acetohydroxy Acid Synthase Coding Gene $ilvBN^M$ for Relieving the Feedback Inhibition by L-Isoleucine The genome of the strain ILE693 is extracted, primers ilvBN-1 and ilvBN-2 are applied to PCR amplification under the conditions that treatment at 94 DEG C is performed for 5 min and 1 cycle, treatment at 94 DEG C is performed for 30 s, treatment at 56 DEG C is performed for 30 s, treatment at 72 DEG C is performed for 1 min and 30 cycles and treatment at 72 DEG C is performed for 10 min and 1 cycle, and the volume of the reaction system is 100 uL. 10 uL of the PCR products is detected through 1.5% agarose gel electrophoresis, a target fragment amplified by PCR is recovered and connected to a pMD™18-T Vector and is then transformed into *E. coli* DH5α competent cells, the cells are applied onto an LB solid culture medium containing ampicillin (100 ug/mL) for inverted culture at 37 DEG C for 24 h, 3 single colonies are picked, and recombinant plasmids are extracted and sequenced.

Sequencing results show that, compared with the wild type ilvBN, the acetohydroxy acid synthase encoded by the mutated gene has mutations of K30Q, A84T, G128S, A226S, K227R, Y252H, T362S and H674L, the mutant is named as $ILVBN^M$, and the coding gene is named as $ilvBN^M$ (as shown in SEQ ID NO. 5).

(6) Comparison of the Enzymatic Characteristics of the Acetohydroxy Acid Synthase Mutant ILVBN$^M$ and the Wild Type Acetohydroxy Acid Synthase ILVBN The genomes of the *Corynebacterium glutamicum* ATCC13032 and the strain ILE693 are taken as templates respectively, primers IV-1 and IV-2 are applied to PCR amplification, the products are recovered and connected to pET-His plasmids digested by BamH I and are then transformed into *Escherichia coli* BL21 (DE3) to obtain strains *E. coli*-ilvBN and *E. coli*-ilvBN$^M$, which are induced by IPTG to express recombinant proteins ILVBN and ILVBN$^M$, bacteria are collected, resuspended in 100 mmol/L potassium phosphate buffer solution (pH=7.8), subjected to ultrasonic disruption and centrifuged, and then the supernatant is collected.

Figure 4:
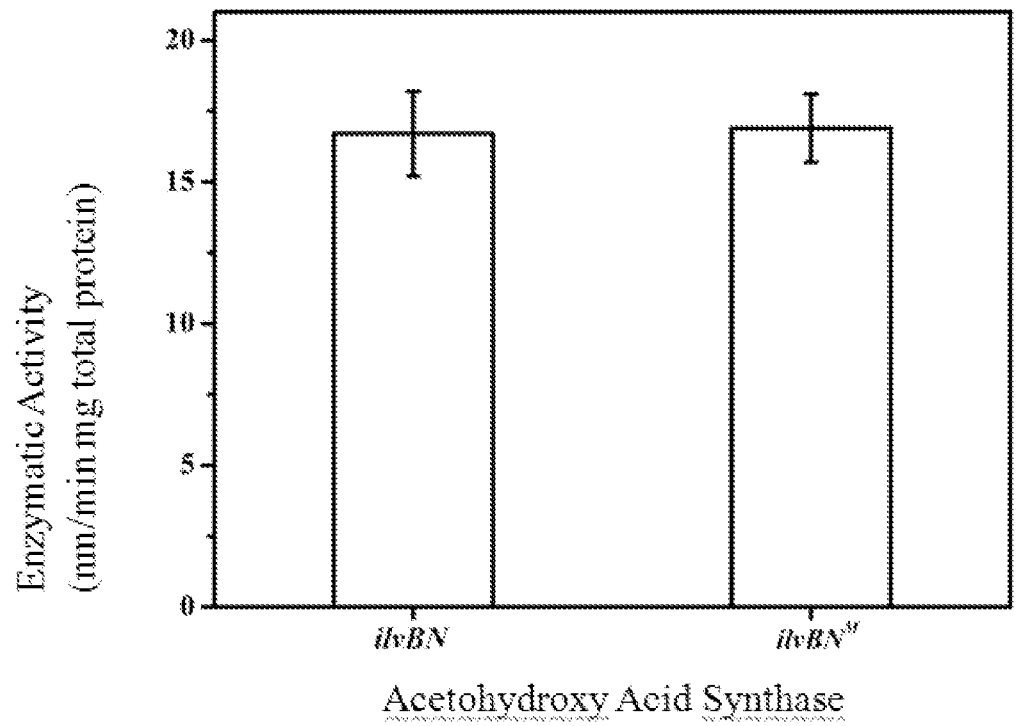
FIG. 4: Comparison of the activity of the acetohydroxy acid synthases(AHAS) encoded by ilvBN$^M$ and ilvBN.

The enzymatic activities of the ILVBN$^M$ and the ILVBN are determined by the following method: adding 100 uL of the above-described supernatant into 1 mL of potassium phosphate buffer solution (100 mmol/L, pH=7.8 and composed of 100 mmol/L sodium pyruvate, 100 mmol/L L2-ketobutyric acid, 10 mmol/L MgCl$_2$ and 0.2 mmol/L thiamine pyrophosphate) for reaction at 37 DEG C for 1 h, adding in 100 uL of sulfuric acid (3 mol/L) for treatment at 65 DEG C for 15 min to terminate the reaction, mixing the reaction solution with 1 mL of 0.5% creatine and 1 mL of α-naphthol solution (containing 2.5 mol/L NaOH) for treatment at 65 DEG C for 20 min, cooling down to room temperature, and measuring the amount of 2-keto-2-hydroxybutyric acid produced (OD$_{525}$) through spectrophotometry. and accordingly calculate the enzymatic activity. As results shown in FIG. 4, the activities of the ILVBN$^M$ and the ILVBN are 16.7 and 16.9 nmol/(min*mg*total protein), respectively, presenting no significant difference.

The influence of the L-isoleucine on the enzymatic activity of the ILVBN$^M$ and the ILVBN is determined by the following method: adding 0, 2, 4, 6, 8, 10 and 12 mmol/L L-isoleucine respectively into the above reaction solution, and then measuring the amount of the produced 2-keto-2-hydroxybutyric acid to study the performance of the ILVBN$^M$ on relieving the feedback inhibition by the L-isoleucine.

Figure 3:
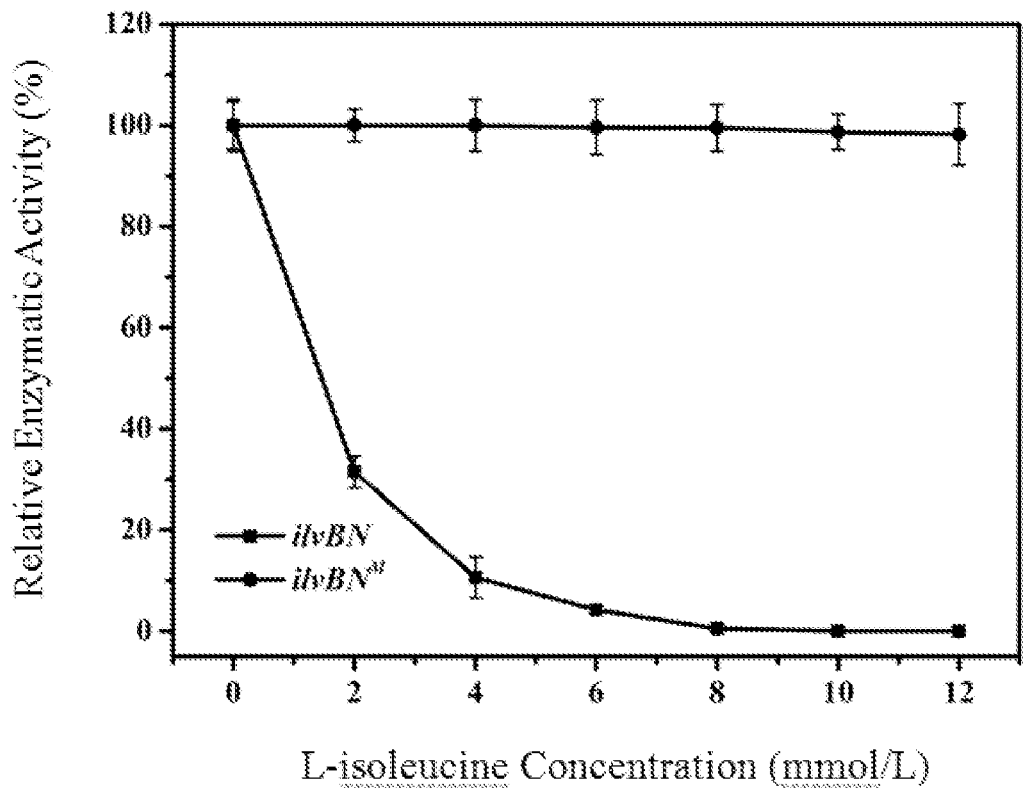
FIG. 3: Influence of L-isoleucine on the activity of the acetohydroxy acid synthases encoded by the genes ilvBN and ilvBN$^M$.

The enzymatic activity when the concentration of the added L-isoleucine is 0 is defined as 100%, compared with which the enzymatic activity of the ILVBN$^M$ or the ILVBN under other L-leucine concentration conditions is the relative enzymatic activity. As shown in FIG. 3, the relative activity of the ILVBN decreases rapidly with increasing L-isoleucine concentration, and when the L-isoleucine concentration is higher than 8 mmol/L, the ILVBN almost presents no activity, indicating that the ILVBN is subject to the feedback inhibition by the L-isoleucine, while the relative enzymatic activity of the mutant ILVBN$^M$ has no significant change with increasing L-leucine concentration, indicating that the ILVBN$^M$ can relieve the feedback inhibition by the L-isoleucine.

It can be seen from the above results, the acetohydroxy acid synthase mutant ILVBN$^M$ relieves the feedback inhibition by the L-leucine and has no significant decrease in the activity compared with the wild type ILVBN.

Embodiment 3: Construction of the L-Leucine Producing Bacterium TE03

(5) Construction of a Recombinant Fragment UHF-leuA$^M$-DHF

An artificially synthesized plasmid containing the gene leuA$^M$ is taken as a template and LEUA-3 and LEUA-4 as primers to perform PCR amplification to obtain the leuA$^M$; The genome of the *Escherichia coli* W3110 is taken as a template and LEUA-1 and LEUA-2 as well as LEUA-5 and LEUA-6 as primers to perform amplification to obtain fragments UHF and DHF, which are the upstream homologous arm and the downstream homologous arm of a gene lad, respectively; UHF, DHF and the leuA$^M$ are taken as templates and LEUA-1 and LEUA-6 as primers to perform PCR amplification, and then recovering is performed to obtain the recombinant fragment UHF-leuA$^M$-DHF.

(6) Construction of a Recombinant Fragment UHFA-ilvBN$^M$ DHFB

A artificially synthesized plasmid containing the gene ilvBN$^M$ is taken as a template and IlvB-3 and IlvB-4 as primers to perform PCR amplification to obtain the ilvBN$^M$; the genome of the *Escherichia coli* W3110 is taken as a template and IlvB-1 and IlvB-2 as well as IlvB-5 and IlvB-6 as primers to perform amplification to obtain fragments UHFA and DHFB, which are the upstream homologous arm and the downstream homologous arm of a gene lacZ, respectively; UHFA, DHFB and the ilvBN$^M$ are taken as templates and IlvBN-1 and IlvBN-6 as primers to perform PCR amplification, and then recovering is performed to obtain the recombinant fragment UHFA-ilvBN$^M$-DHFB.

(7) Construction of a Recombinant Plasmid pTR-leuBCD

The genome of the *Escherichia coli* W3110 is taken as a template and leuBCD-1 and leuBCD-2 as primers to perform PCR amplification to obtain leuBCD (an operon composed of leuB and leuCD in the *Escherichia coli*), and a plasmid pTrc99a is subjected to digestion by BamH I, electrophoresis and gel extraction and is then connected to the leuBCD to obtain the recombinant plasmid pTR-leuBCD.

(8) Construction of the L-Leucine Genetically Engineered Bacterium TE03

PG-1 and PG-2, PG-3 and PG-4 are respectively annealed at 52 DEG C and then connected to plasmids pGRB to obtain pGRB1 and pGRB2, wherein PG-1 and PG-2 as well as PG-3 and PG-4 are single-stranded DNAs of guide sequences for Cas9 to identify the lacI and lacZ gene sequences of the genome of the W3110, and the single-stranded DNAs are annealed to double-stranded DNAs which can be connected with the pGRB. The pREDCas9 plasmids are transformed into the *Escherichia coli* W3110, and positive clones are selected to obtain a W3110-pREDCas9 strain. The pGRB1 and the UHF-leuA$^M$-DHF are respectively transformed into the W3110-pREDCas9, positive clones are selected and subjected to elimination of pGRB-gRNA and the pREDCas9 plasmids to obtain a TE01 strain. In the same way, the pGRB2 and the UHFA-ilvBN$^M$-DHFB are transformed into the TE01 containing the pREDCas9 to obtain a TE02 strain. The pTR-leuBCD is transformed into the TE02 to obtain the TE03.

Embodiment 4: Fermentation Experiment of the L-Leucine Producing Bacterium TE03 in a Fermentation Tank (4) Seed Culture 3-5 tubes of fresh slant activated TE03 are inoculated by an inoculating loop into a 5 L fermentation tank filled with 1 L of a seed culture medium, the pH of the fermentation liquid is regulated to 6.5-7.5 by batch-feeding 25% (W/V) ammonia liquor, the content of dissolved oxygen is maintained to be 20-50%, the ventilating rate is 3-5 m3/h, the stirring velocity is 400-500 rpm, and culture is performed at 32 DEG C for 6-8 h.

(5) Fermentation in the Fermentation Tank

Figure 5:
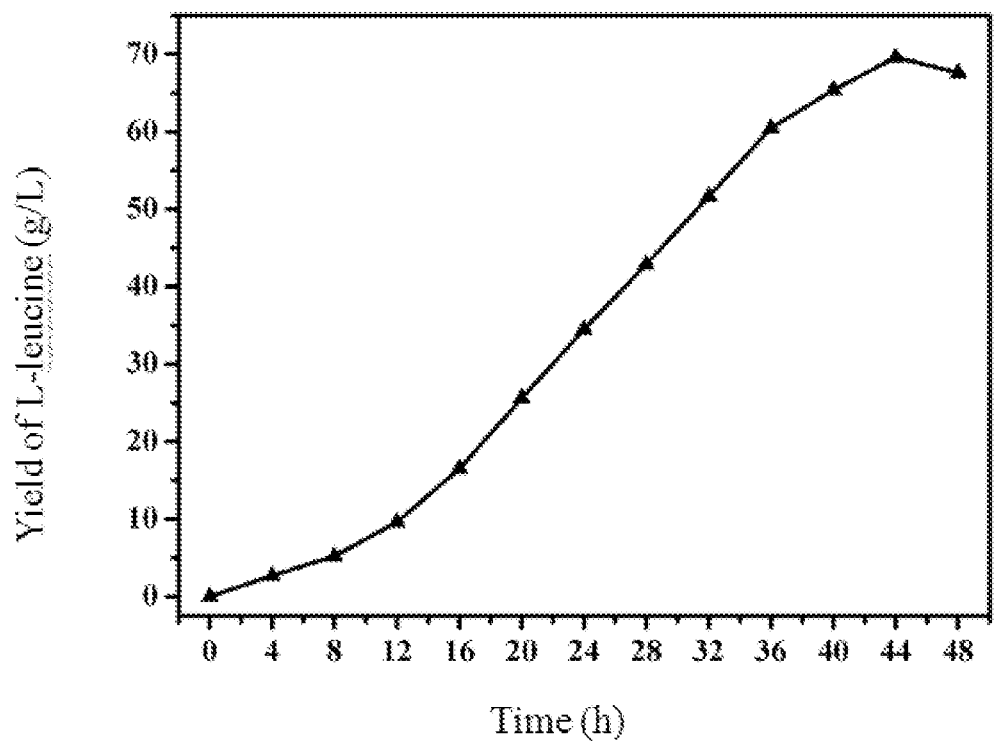
FIG. 5: The process curve of fermentation of the L-leucine genetically engineered bacterium strain TE03.

The seed culture obtained in the step (1) is inoculated at an inoculum size of 5% to a 5 L fermentation tank filled with 3 L of a fermentation culture medium for tank fermentation, the fermentation temperature is 35 DEG C, the ventilating rate is 3-5 m3/h, the stirring velocity is 600 rpm, the content of dissolved oxygen is maintained to be 20-40%, an 80% (W/V) glucose solution is batch-fed to maintain the residual sugar concentration to be 0.1-0.5% (W/V), the pH of the fermentation liquid is regulated to 6.5-7.5 by batch-feeding 25% (W/V) ammonia water and the fermentation is performed for 48 h (the process curve of fermentation is shown as FIG. 5).

(6) Detection of L-Leucine in the Fermentation Liquid

The detection method is the same as that in the step 1.7 of (1) of the embodiment 1, and according to the detection, after the fermentation is performed for 44 h, the yield of L-leucine reaches the highest 69.6 g/L at 69.6 g/L with a conversion rate of 19.1%.

The seed culture medium is composed of:

14 g/L glucose, 5 g/L peptone, 3 g/L yeast powder, 2 g/L KH$_2$PO$_4$, 1 g/L MgSO$_4$, 10 mg/L FeSO$_4$ and 10 mg/L MnSO$_4$, the pH is 7.0, and the seed culture medium is subjected to high-pressure steam sterilization at 0.075 MPa for 15 min.

The fermentation culture medium is composed of:

25 g/L glucose, 12 g/L peptone, 4 g/L yeast powder, 3.5 g/L KH$_2$PO$_4$, 1.5 g/L MgSO$_4$, 15 mg/L FeSO$_4$, 15 mg/L MnSO$_4$ and 0.01 mg/L VB1, the pH is 7.0, and the fermentation culture medium is subjected to high-pressure steam sterilization at 0.075 MPa for 15 min.

Embodiment 5: Influence of Overexpression of leuA$^M$ on L-Leucine Synthesis

Figure 6:
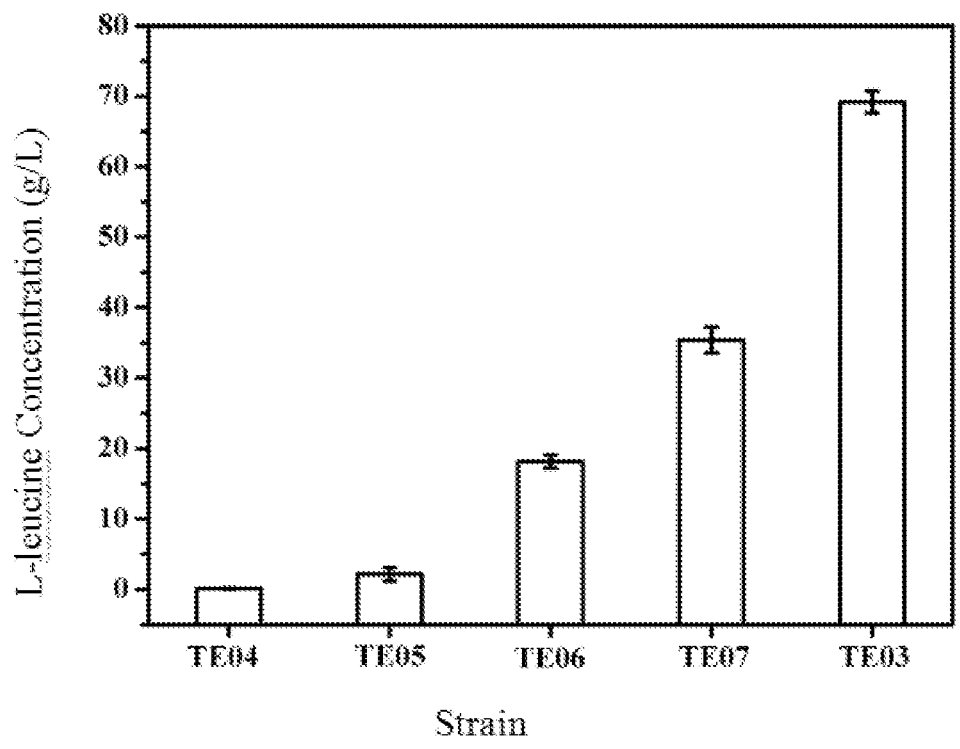
FIG. 6: Influence of overexpression of leuA$^M$ on L-leucine synthesis.

A method identical to that in the embodiment 1 is applied to respectively constructing strains: 1) an ilvBN$^M$ and leuBCD overexpressing strain TE04, 2) an ilvBN, leuA and leuBCD overexpressing strain TE05, 3) an ilvBN$^M$, leuA and leuBCD overexpressing strain TE06 and 4) an ilvBN, leuA$^M$ and leuBCD overexpressing strain TE07. A method identical to that in the embodiment 4 is applied to performing fermentation experiments. Detection results show that, after 44 h of fermentation, the strain TE03 has the highest yield of L-leucine (69.2 g/L), followed by strain TE07 (35.37 g/L) and strain TE06 (18.16 g/L), and strain TE04 and strain TE05 are the lowest (0.12 and 2.15 g/L, respectively) (as shown in FIG. 6).

Above-described are merely several embodiments of the present invention, which are described specifically in detail but cannot be construed as limitation to the scope of the patent. It should be noted that, for those skilled in the art, modifications, combinations and improvements can be made on the described embodiments without departing from the concept of the patent and all fall into the scope of protection of the patent. Therefore, the scope of protection of the patent should be subject to the claims.

---

We claim:

1. A genetically engineered bacterium for producing L-leucine, the genetically engineered bacterium is obtained by overexpressing a gene leuA$^M$ encoding 2-isopropyl malate synthase, a gene ilvBN$^M$ encoding acetohydroxy acid synthase for relieving feedback inhibition by L-isoleucine, a gene leuB encoding 3-isopropyl malate dehydrogenase and a gene leuCD encoding 3-isopropyl malate dehydratase in a host cell, wherein the nucleotide sequence of the gene leuA$^M$ is shown as SEQ ID NO. 2.

2. The genetically engineered bacterium for producing the L-leucine according to claim 1, characterized in that, the host cell is selected from the group consisting of Escherichia coli, Corynebacterium glutamicum, Bacillus subtilis, Bacillus megaterium, Bacillus amyloliquefaciens, Vibrio natriegens and Saccharomyces cerevisiae.

3. The genetically engineered bacterium for producing the L-leucine according to claim 1, characterized in that, an acetohydroxy acid synthase encoded by the gene relieves the feedback inhibition by the L-isoleucine and has a nucleotide sequence shown as SEQ ID NO. 5.

4. The genetically engineered bacterium for producing the L-leucine according to claim 1, characterized in that, the genetically engineered bacterium is obtained by using Escherichia coli W3110 as the host cell to overexpress the gene leuA$^M$ as shown in SEQ ID NO. 2, the gene ilvBN$^M$ as shown in SEQ ID NO. 5 and the gene leuBCD as shown in SEQ ID NO. 6.

5. The genetically engineered bacterium for producing the L-leucine according to claim 1, characterized in that, constructed by the following syeps:
(1) separately amplifying the genes leuA$^M$, leuB, leuCD and ilvBN$^M$, and constructing genome integration fragments;
(2) sequentially expressing the genome integration fragments constructed in step (1) and a recombinant plasmid in the host cell by a CRISPR/Cas9 gene editing technology.

6. The genetically engineered bacterium for producing the L-leucine according to claim 1, used in the production of L-leucine.

7. The genetically engineered bacterium for producing the L-leucine according to claim 6, characterized in that, a method for synthesizing the L-leucine with the genetically engineered bacterium through fermentation includes:
inoculating a seed culture at an inoculum size of 5-10% onto a fermentation culture medium for fermentation culture, wherein the content of dissolved oxygen is maintained at 20-40%, the pH is maintained at 6.5-7.5, the culture temperature is 30-35° C., the fermentation period is 40-48 h, and the residual sugar concentration is maintained at 0-0.4% W/V during the fermentation; the fermentation culture medium is composed of 25 g/L glucose, 12 g/L peptone, 4 g/L yeast powder, 3.5 g/L $KH_2PO_4$, 1.5 g/L $MgSO_4$, 15 mg/L $FeSO_4$, 15 mg/L $MnSO_4$ and 0.01 mg/L VB1 (Vitamin B1); the pH of the fermentation culture medium is 7.0, the pressure is 0.075 MPa, and the fermentation culture medium is subjected to high-pressure steam sterilization for 15 min.

8. The genetically engineered bacterium for producing the L-leucine according to claim 2, characterized in that, the host cell is *Escherichia coli*.

9. The genetically engineered bacterium for producing the L-leucine according to claim 2, characterized in that, the gene leuB is the gene with Genbank accession number of b0073.

10. The genetically engineered bacterium for producing the L-leucine according to claim 2, characterized in that, the gene leuCD is the gene with Genbank accession number of b0072.

11. The genetically engineered bacterium for producing the L-leucine according to claim 2, characterized in that, the gene leuBCD has a nucleotide sequence as shown in SEQ ID NO. 6.

\* \* \* \* \*

SEQUENCE LISTING

```
<160> NUMBER OF SEQ ID NOS: 36

<210> SEQ ID NO 1
<211> LENGTH: 616
<212> TYPE: PRT
<213> ORGANISM: Artificial Sequence
<220> FEATURE:
<223> OTHER INFORMATION: The sequence is synthesized.

<400> SEQUENCE: 1

Met Ser Pro Asn Asp Ala Leu Ile Ser Ala Pro Ala Lys Phe Glu Thr
1               5                   10                  15

Pro Val Gly Pro Arg Asn Glu Gly Gln Pro Ala Trp Asn Lys Gln Arg
            20                  25                  30

Gly Ser Ser Met Pro Val Asn Arg Tyr Met Pro Phe Glu Val Glu Val
        35                  40                  45

Glu Asp Ser Ser Leu Pro Asp Arg Thr Trp Pro Asp Lys Lys Ile Thr
    50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Arg Met Phe Glu Leu
                85                  90                  95

Leu Val Gln Met Gly Phe Lys Glu Ile Glu Val Gly Phe Pro Ser Ala
            100                 105                 110

Ser Gln Thr Asp Phe Asp Phe Val Arg Glu Ile Ile Glu Lys Asp Met
        115                 120                 125

Ile Pro Asp Asp Val Thr Ile Gln Val Leu Val Gln Ala Arg Glu His
    130                 135                 140

Leu Ile Arg Arg Thr Phe Glu Ala Cys Glu Gly Ala Lys Asn Val Ile
145                 150                 155                 160
```

-continued

```
Val His Phe Tyr Asn Ser Thr Ser Ile Leu Gln Arg Asn Val Val Phe
            165                 170                 175

Arg Met Asp Lys Val Gln Val Lys Lys Leu Ala Thr Asp Ala Ala Glu
            180                 185                 190

Leu Ile Lys Thr Val Ala Gln Asp Tyr Pro Asp Thr Asn Trp Arg Trp
            195                 200                 205

Gln Tyr Ser Pro Glu Ser Phe Thr Gly Thr Glu Val Glu Tyr Ala Lys
            210                 215                 220

Glu Val Val Asp Ala Val Glu Val Met Asp Pro Thr Pro Glu Asn
225                 230                 235                 240

Pro Met Ile Ile Asn Leu Pro Ser Thr Val Glu Met Ile Thr Pro Asn
            245                 250                 255

Val Tyr Ala Asp Ser Ile Glu Trp Met His Arg Asn Leu Asn Arg Arg
            260                 265                 270

Asp Ser Ile Ile Leu Ser Leu His Pro His Asn Asp Arg Gly Thr Gly
            275                 280                 285

Val Gly Ala Ala Glu Leu Gly Tyr Met Ala Gly Ala Asp Arg Ile Glu
            290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
            325                 330                 335

Phe Thr Asp Ile Arg Gln Ile Arg Ser Thr Val Glu Tyr Cys Asn Gln
            340                 345                 350

Leu Arg Val Pro Glu Arg His Pro Tyr Gly Gly Asp Leu Val Phe Thr
            355                 360                 365

Ala Leu Ser Gly Ser His Gln Asp Ala Val Asn Met Gly Leu Asp Ala
            370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
            405                 410                 415

Pro Lys Asp Val Gly Arg Asp Tyr Glu Ala Val Ile Arg Val Asn Ser
            420                 425                 430

Gln Ser Gly Lys Gly Val Ala Tyr Ile Met Lys Thr Asp His Gly
            435                 440                 445

Leu Gln Ile Pro Arg Ser Met Gln Val Glu Phe Ser Thr Val Val Gln
            450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
            485                 490                 495

Ile Ala Leu Arg Val Glu Asn Ala Gln Thr Glu Asn Glu Asp Ala Ser
            500                 505                 510

Ile Thr Ala Glu Leu Ile His Asn Gly Lys Asp Val Thr Val Asp Gly
            515                 520                 525

His Gly Asn Gly Pro Leu Ala Ala Tyr Ala Asn Ala Leu Glu Lys Leu
            530                 535                 540

Gly Ile Asp Val Glu Ile Gln Glu Tyr Asn Gln His Ala Arg Thr Ser
545                 550                 555                 560

Asp Asp Asp Ala Glu Ala Ala Tyr Val Leu Ala Glu Val Asn Gly
            565                 570                 575

Arg Lys Val Trp Gly Val Gly Ile Ala Gly Ser Ile Thr Tyr Ala Ser
```

```
              580                 585                 590
Leu Lys Ala Ala Thr Ser Ala Val Asn Arg Ala Leu Asp Val Asn His
        595                 600                 605

Glu Ala Val Leu Ala Gly Gly Val
        610                 615

<210> SEQ ID NO 2
<211> LENGTH: 1851
<212> TYPE: DNA
<213> ORGANISM: Artificial Sequence
<220> FEATURE:
<223> OTHER INFORMATION: The sequence is synthesized.

<400> SEQUENCE: 2
atgtctccta acgatgcatt gatctccgca cctgccaagt tcgaaacccc agttgggcct        60
cgcaacgaag gccagccagc atggaataag cagcgtggct cctcaatgcc agttaaccgc       120
tacatgcctt tcgaggttga ggtagaagat agttctctgc cggaccgcac ttggccagat       180
aaaaaaatca ccgttgcacc tcagtggtgt gctgttgacc tgcgtgacgg caaccaggct       240
ctgattgatc cgatgtctcc tgagcgtaag cgccgcatgt ttgagctgct ggttcagatg       300
ggcttcaaag aaatcgaggt cggttttccct tcagcttccc agactgattt tgatttcgtt       360
cgtgagatca tcgaaaagga catgatccct gacgatgtca ccattcaggt tctggttcag       420
gctcgtgagc acctgattcg ccgtactttt gaagcttgcg aaggcgcaaa aaacgttatc       480
gtgcacttct acaactccac ctccatcctg cagcgcaacg tggtgttccg catggacaag       540
gtgcaggtga agaagctggc taccgatgcc gctgaactaa tcaagaccgt cgctcaggat       600
tacccagaca ccaactggcg ctggcagtac tcccctgagt ccttcaccgg cactgaggtt       660
gagtacgcca aggaagttgt ggacgcagtt gttgaggtca tggatccaac tcctgagaac       720
ccaatgatca tcaacctgcc ttccaccgtt gagatgatca cccctaacgt ttacgcagac       780
tccattgaat ggatgcaccg caatctaaac cgtcgtgatt ccattatcct gtccctgcac       840
ccgcacaatg accgtggcac cggcgttggc gcagctgagc tgggctacat ggctggcgct       900
gaccgcatcg aaggctgcct gttcggcaac ggcgagcgca ccggcaacgt ctgcctggtc       960
accctggcac tgaacatgct gacccagggc gttgaccctc agctggactt caccgatata      1020
cgccagatcc gcagcaccgt tgaatactgc aaccagctgc gcgttcctga gcgccaccca      1080
tacggcggtg acctggtctt caccgctctc tccggttccc caggacgcg tgtgaacatg      1140 ggtctggacg ccatggctgc caaggttcag ccaggtgcta gctccactga gtttcttgg      1200 gaacagctgc gcgacaccga atgggaggtt ccttacctgc ctatcgatcc aaaggatgtc      1260
ggtcgcgact acgaggctgt tatccgcgtg aactccagt ccggcaaggg cggcgttgct      1320
tacatcatga agaccgatca cggtctgcag atccctcgct ccatgcaggt tgagttctcc      1380
accgttgtcc agaacgtcac cgacgctgag ggcggcgagg tcaactccaa ggcaatgtgg      1440
gatatcttcg ccaccgagta cctggagcgc accgcaccag ttgagcagat cgcgctgcgc      1500
gtcgagaacg ctcagaccga aaacgaggat gcatccatca ccgccgagct catccacaac      1560
ggcaaggacg tcaccgtcga tggccacggc aacggcccac tggccgctta cgccaacgcg      1620
ctggagaagc tgggcatcga cgttgagatc caggaataca ccagcacgc ccgcacctcg      1680 gacgacgatg cagaagcagc cgcctacgtg ctggctgagg tcaacggccg caaggtctgg      1740
ggcgtcggca tcgctggctc catcacctac gcttcgctga aggcagcgac ctccgccgta      1800
aaccgcgcgc tggacgtcaa ccacgaggca gtcctggctg gcggcgtcta a              1851
```

<210> SEQ ID NO 3
<211> LENGTH: 616
<212> TYPE: PRT
<213> ORGANISM: Corynebacterium glutamicum ATCC13032

<400> SEQUENCE: 3

```
Met Ser Pro Asn Asp Ala Phe Ile Ser Ala Pro Ala Lys Ile Glu Thr
1               5                   10                  15
Pro Val Gly Pro Arg Asn Glu Gly Gln Pro Ala Trp Asn Lys Gln Arg
            20                  25                  30
Gly Ser Ser Met Pro Val Asn Arg Tyr Met Pro Phe Glu Val Glu Val
        35                  40                  45
Glu Asp Ile Ser Leu Pro Asp Arg Thr Trp Pro Asp Lys Lys Ile Thr
    50                  55                  60
Val Ala Pro Gln Trp Cys Ala Val Asp Leu Arg Asp Gly Asn Gln Ala
65                  70                  75                  80
Leu Ile Asp Pro Met Ser Pro Glu Arg Lys Arg Met Phe Glu Leu
                85                  90                  95
Leu Val Gln Met Gly Phe Lys Glu Ile Glu Val Gly Phe Pro Ser Ala
            100                 105                 110
Ser Gln Thr Asp Phe Asp Phe Val Arg Glu Ile Ile Glu Lys Gly Met
        115                 120                 125
Ile Pro Asp Asp Val Thr Ile Gln Val Leu Val Gln Ala Arg Glu His
    130                 135                 140
Leu Ile Arg Arg Thr Phe Glu Ala Cys Glu Gly Ala Lys Asn Val Ile
145                 150                 155                 160
Val His Phe Tyr Asn Ser Thr Ser Ile Leu Gln Arg Asn Val Val Phe
                165                 170                 175
Arg Met Asp Lys Val Gln Val Lys Lys Leu Ala Thr Asp Ala Ala Glu
            180                 185                 190
Leu Ile Lys Thr Ile Ala Gln Asp Tyr Pro Asp Thr Asn Trp Arg Trp
        195                 200                 205
Gln Tyr Ser Pro Glu Ser Phe Thr Gly Thr Glu Val Glu Tyr Ala Lys
    210                 215                 220
Glu Val Val Asp Ala Val Val Glu Val Met Asp Pro Thr Pro Glu Asn
225                 230                 235                 240
Pro Met Ile Ile Asn Leu Pro Ser Thr Val Glu Met Ile Thr Pro Asn
                245                 250                 255
Val Tyr Ala Asp Ser Ile Glu Trp Met His Arg Asn Leu Asn Arg Arg
            260                 265                 270
Asp Ser Ile Ile Leu Ser Leu His Pro His Asn Asp Arg Gly Thr Gly
        275                 280                 285
Val Gly Ala Ala Glu Leu Gly Tyr Met Ala Gly Ala Asp Arg Ile Glu
    290                 295                 300
Gly Cys Leu Phe Gly Asn Gly Glu Arg Thr Gly Asn Val Cys Leu Val
305                 310                 315                 320
Thr Leu Ala Leu Asn Met Leu Thr Gln Gly Val Asp Pro Gln Leu Asp
                325                 330                 335
Phe Thr Asp Ile Arg Gln Ile Arg Ser Thr Val Glu Tyr Cys Asn Gln
            340                 345                 350
Leu Arg Val Pro Glu Arg His Pro Tyr Gly Gly Asp Leu Val Phe Thr
        355                 360                 365
Ala Phe Ser Gly Ser His Gln Asp Ala Val Asn Lys Gly Leu Asp Ala
```

```
Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
            405                 410                 415

Pro Lys Asp Val Gly Arg Asp Tyr Glu Ala Val Ile Arg Val Asn Ser
        420                 425                 430

Gln Ser Gly Lys Gly Val Ala Tyr Ile Met Lys Thr Asp His Gly
        435                 440                 445

Leu Gln Ile Pro Arg Ser Met Gln Val Glu Phe Ser Thr Val Val Gln
    450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
            500                 505                 510

Ile Thr Ala Glu Leu Ile His Asn Gly Lys Asp Val Thr Val Asp Gly
        515                 520                 525

Arg Gly Asn Gly Pro Leu Ala Ala Tyr Ala Asn Ala Leu Glu Lys Leu
    530                 535                 540

Gly Ile Asp Val Glu Ile Gln Glu Tyr Asn Gln His Ala Arg Thr Ser
545                 550                 555                 560

Gly Asp Asp Ala Glu Ala Ala Tyr Val Leu Ala Glu Val Asn Gly
                565                 570                 575

Arg Lys Val Trp Gly Val Gly Ile Ala Gly Ser Ile Thr Tyr Ala Ser
            580                 585                 590

Leu Lys Ala Val Thr Ser Ala Val Asn Arg Ala Leu Asp Val Asn His
        595                 600                 605

Glu Ala Val Leu Ala Gly Gly Val
    610                 615

<210> SEQ ID NO 4
<211> LENGTH: 1851
<212> TYPE: DNA
<213> ORGANISM: Corynebacterium glutamicum ATCC13032

<400> SEQUENCE: 4
atgtctccta cgatgcatt catctccgca cctgccaaga tcgaaacccc agttgggcct      60
cgcaacgaag ccagccagc atggaataag cagcgtggct cctcaatgcc agttaaccgc    120
tacatgcctt cgaggttga ggtagaagat atttctctgc cggaccgcac ttggccagat    180
aaaaaaatca ccgttgcacc tcagtggtgt gctgttgacc tcgtgacgg caaccaggct    240 ctgattgatc cgatgtctcc tgagcgtaag cgccgcatgt tgagctgct ggttcagatg    300 ggcttcaaag aaatcgaggt cggtttccct tcagcttccc agactgattt tgatttcgtt    360
cgtgagatca tcgaaaaggg catgatccct gacgatgtca ccattcaggt tctggttcag    420
gctcgtgagc acctgattcg ccgtactttt gaagcttgcg aaggcgcaaa aaacgttatc    480
gtgcacttct acaactccac ctccatcctg cagcgcaacg tggtgttccg catggacaag    540
gtgcaggtga agaagctggc taccgatgcc gctgaactaa tcaagaccat cgctcaggat    600
tacccagaca ccaactggcg ctggcagtac tcccctgagt ccttcaccgg cactgaggtt    660
gagtacgcca aggaagttgt ggacgcagtt gttgaggtca tggatccaac tcctgagaac    720
```

| | |
|---|---|
| ccaatgatca tcaacctgcc ttccaccgtt gagatgatca cccctaacgt ttacgcagac | 780 |
| tccattgaat ggatgcaccg caatctaaac cgtcgtgatt ccattatcct gtccctgcac | 840 |
| ccgcacaatg accgtggcac cggcgttggc gcagctgagc tgggctacat ggctggcgct | 900 |
| gaccgcatcg aaggctgcct gttcggcaac ggcgagcgca ccggcaacgt ctgcctggtc | 960 |
| accctggcac tgaacatgct gacccagggc gttgaccctc agctggactt caccgatata | 1020 |
| cgccagatcc gcagcaccgt tgaatactgc aaccagctgc gcgttcctga gcgccaccca | 1080 |
| tacggcggtg acctggtctt caccgctttc tccggttccc accaggacgc tgtgaacaag | 1140 |
| ggtctggacg ccatggctgc caaggttcag ccaggtgcta gctccactga gtttcttgg | 1200 |
| gagcagctgc gcgacaccga atgggaggtt ccttacctgc ctatcgatcc aaaggatgtc | 1260 |
| ggtcgcgact acgaggctgt tatccgcgtg aactcccagt ccggcaaggg cggcgttgct | 1320 |
| tacatcatga agaccgatca cggtctgcag atccctcgct ccatgcaggt tgagttctcc | 1380 |
| accgttgtcc agaacgtcac cgacgctgag ggcggcgagg tcaactccaa ggcaatgtgg | 1440 |
| gatatcttcg ccaccgagta cctggagcgc accgcaccag ttgagcagat cgcgctgcgc | 1500 |
| gtcgagaacg ctcagaccga aaacgaggat gcatccatca ccgccgagct catccacaac | 1560 |
| ggcaaggacg tcaccgtcga tggccgcggc aacggcccac tggccgctta cgccaacgcg | 1620 |
| ctggagaagc tgggcatcga cgttgagatc caggaataca accagcacgc ccgcacctcg | 1680 |
| ggcgacgatg cagaagcagc cgcctacgtg ctggctgagg tcaacggccg caaggtctgg | 1740 |
| ggcgtcggca tcgctggctc catcacctac gcttcgctga aggcagtgac ctccgccgta | 1800 |
| aaccgcgcgc tggacgtcaa ccacgaggca gtcctggctg gcggcgttta a | 1851 |

```
<210> SEQ ID NO 5
<211> LENGTH: 2413
<212> TYPE: DNA
<213> ORGANISM: Artificial Sequence
<220> FEATURE:
<223> OTHER INFORMATION: The sequence is synthesized.

<400> SEQUENCE: 5
```

| | |
|---|---|
| gtgaatgtgg cagcttctca acagcccact cccgccacgg ttgcaagccg tggtcgatcc | 60 |
| gccgcccctg agcggatgac aggtgcacag gcaattgttc gatcgctcga ggagcttaac | 120 |
| gccgacatcg tgttcggtat tcctggtggt gcggtgctac cggtgtatga cccgctctat | 180 |
| tcctccacaa aggtgcgcca cgtcttggtg cgccacgagc agggcgcagg ccacgcagca | 240 |
| accggctaca cgcaggttac tggacgcgtt ggcgtctgca ttgcaacctc tggcccagga | 300 |
| gcaaccaact tggttacccc aatcgctgat gcaaacttgg actccgttcc catggttgcc | 360 |
| atcaccggcc aggtcggaag tagcctgctg ggtaccgacg ctttccagga agccgatatc | 420 |
| cgcggcatca ccatgccagt gaccaagcac aacttcatgg tcaccaaccc taacgacatt | 480 |
| ccacaggcat ggctgaggc attccacctc gcgattactg gtcgcccgg ccctgttctg | 540 |
| gtggatattc ctaaggatgt ccagaacgct gaattggatt tcgtctggcc accaaagatc | 600 |
| gacctgccag gctaccgccc agtttcaaca ccacatgctc gccagatcga gcaggcagtc | 660 |
| aagctgatcg gtgagtctag gaagcccgtc ctttacgttg gtggtggcgt aatcaaggct | 720 |
| gacgcacacg aagagcttcg tgcgttcgct gagcacaccg gcatcccagt tgtcaccacc | 780 |
| ttgatggctt tgggtacttt cccagagtct cacgagctgc acatgggtat gccaggcatg | 840 |
| catggcactg tgtccgctgt tggtgcactg cagcgcagcg acctgctgat tgctatcggc | 900 |
| tcccgctttg atgaccgcgt caccggtgac gttgacacct tcgcgcctga cgccaagatc | 960 |

```
attcacgccg acattgatcc tgccgaaatc ggcaagatca agcaggttga ggttccaatc    1020
gtgggcgatg cccgcgaagt tcttgctcgt ctgctggaaa ccaccaaggc aagcaaggca    1080
gagtctgagg acatctccga gtgggttgac tacctcaagg gcctcaaggc acgtttcccg    1140
cgtggctacg acgagcagcc aggcgatctg ctggcaccac agtttgtcat tgaaaccctg    1200
tccaaggaag ttggccccga cgcaatttac tgcgccggcg ttggccagca ccaaatgtgg    1260
gcagctcagt tcgttgactt tgaaaagcca cgcacctggc tcaactccgg tggactgggc    1320
accatgggct acgcagttcc tgcggcccct tggagcaaagg ctggcgcacc tgacaaggaa    1380
gtctgggcta cgacggcga cggctgtttc cagatgacca accaggaact caccaccgcc    1440
gcagttgaag gtttccccat taagatcgca ctaatcaaca acggaaacct gggcatggtt    1500
cgccaatggc agaccctatt ctatgaagga cggtactcaa atactaaact tcgtaaccag    1560
ggcgagtaca tgcccgactt tgttaccctt tctgagggac ttggctgtgt tgccatccgc    1620
gtcaccaaag cggaggaagt actgccagcc atccaaaagg ctcgagagat caacgaccgc    1680
ccagtagtca tcgacttcat cgtcggtgaa gacgcacagg tatggccaat ggtgtctgct    1740
ggatcatcca actccgatat ccagtacgca ctcggattgc gcccattctt tgatggtgat    1800
gaatctgcag cagaagatcc tgccgacatt cacgaagccg tcagcgacat tgatgccgcc    1860
gttgaatcga ccgaggcata aggagagacc caagatggct aatttctgacg tcacccgcca    1920
catcctgtcc gtactcgttc aggacgtaga cggaatcatt tcccgcgtat caggtatgtt    1980
cacccgacgc gcattcaacc tcgtgtccct cgtgtctgca aagaccgaaa cactcggcat    2040
caaccgcatc acggttgttg tcgacgccga cgagctcaac attgagcaga tcaccaagca    2100
gctcaacaag ctgatccccg tgctcaaagt cgtgcgactt gatgaagaga ccactatcgc    2160
ccgcgcaatc atgctggtta aggtctctgc ggacagcacc aaccgtccgc agatcgtcga    2220
cgccgcgaac atcttccgcg cccgagtcgt cgacgtggct ccagactctg tggttattga    2280
atccacaggc accccaggca agctccgcgc actgcttgac gtgatggaac cattcggaat    2340
ccgcgaactg atccaatccg gacagattgc actcaaccgc ggtccgaaga ccatggctcc    2400
ggccaagatc taa                                                       2413

<210> SEQ ID NO 6
<211> LENGTH: 3111
<212> TYPE: DNA
<213> ORGANISM: Escherichia coli

<400> SEQUENCE: 6
atgtcgaaga attaccatat tgccgtattg ccggggacg gtattggtcc ggaagtgatg     60
acccaggcgc tgaaagtgct ggatgccgtg cgcaaccgct tgcgatgcg catcaccacc    120
agccattacg atgtaggcgg cgcagccatt gataaccacg ggcaaccact gccgcctgcg    180
acggttgaag gttgtgagca agccgatgcc gtgctgtttg gctcggtagg cggcccgaag    240
tgggaacatt taccaccaga ccagcaacca gaacgcggcg cgctgctgcc tctgcgtaag    300
cacttcaaat tattcagcaa cctgcgcccg gcaaaactgt atcaggggct ggaagcattc    360
tgtccgctgc gtgcagacat tgccgcaaac ggcttcgaca tcctgtgtgt gcgcgaactg    420
accggcggca tctatttcgg tcagccaaaa ggccgcgaag tagcggaca atatgaaaaa    480
gcctttgata ccgaggtgta tcaccgtttt gagatcgaac gtatcgcccg catcgcgttt    540
gaatctgctc gcaagcgtcg ccacaaagtg acgtcgatcg ataaagccaa cgtgctgcaa    600
```

```
tcctctattt tatggcggga gatcgttaac gagatcgcca cggaataccc ggatgtcgaa      660
ctggcgcata tgtacatcga caacgccacc atgcagctga ttaaagatcc atcacagttt      720
gacgttctgc tgtgctccaa cctgtttggc gacattctgt ctgacgagtg cgcaatgatc      780
actggctcga tggggatgtt gccttccgcc agcctgaacg agcaaggttt tggactgtat      840
gaaccggcgg gcggctcggc accagatatc gcaggcaaaa acatcgccaa cccgattgca      900
caaatccttt cgctggcact gctgctgcgt tacagcctgg atgccgatga tgcggcttgc      960
gccattgaac gcgccattaa ccgcgcatta aagaaggca ttcgcaccgg ggatttagcc     1020
cgtggcgctg ccgccgttag taccgatgaa atgggcgata tcattgcccg ctatgtagca     1080
gaaggggtgt aatcatggct aagacgttat acgaaaaatt gttcgacgct cacgttgtgt     1140
acgaagccga aaacgaaacc ccactgttat atatcgaccg ccacctggtg catgaagtga     1200
cctcaccgca ggcgttcgat ggtctgcgcg cccacggtcg cccggtacgt cagccgggca     1260
aaaccttcgc taccatggat cacaacgtct ctacccagac caaagacatt aatgcctgcg     1320
gtgaaatggc gcgtatccag atgcaggaac tgatcaaaaa ctgcaaagaa tttggcgtcg     1380
aactgtatga cctgaatcac ccgtatcagg ggatcgtcca cgtaatgggg ccggaacagg     1440
gcgtcacctt gccggggatg accattgtct gcggcgactc gcataccgcc acccacggcg     1500
cgtttggcgc actggccttt ggtatcggca cttccgaagt tgaacacgta ctggcaacgc     1560
aaaccctgaa cagggccgc gcaaaaacca tgaaaattga agtccagggc aaagccgcgc     1620
cgggcattac cgcaaaagat atcgtgctgg caattatcgg taaaaccggt agcgcaggcg     1680
gcaccgggca tgtggtggag ttttgcgcg aagcaatccg tgatttaagc atggaaggtc     1740 gtatgacccct gtgcaatatg gcaatcgaaa tgggcgcaaa agccggtctg gttgcaccgg     1800
acgaaaccac ctttaactat gtcaaaggcc gtctgcatgc cccgaaaggc aaagatttcg     1860
acgacgccgt tgcctactgg aaaaccctgc aaaccgacga aggcgcaact ttcgataccg     1920
ttgtcactct gcaagcagaa gaaatttcac cgcaggtcac ctggggcacc aatcccggcc     1980
aggtgatttc cgtgaacgac aatattcccg atccggcttc gtttgccgat ccggttgaac     2040
gcgcgtcggc agaaaaagcg ctggcctata tggggctgaa accgggtatt ccgctgaccg     2100
aagtggctat cgacaaagtg tttatcggtt cctgtaccaa ctcgcgcatt gaagatttac     2160
gcgcggcagc ggagatcgcc aaagggcgaa aagtcgcgcc aggcgtgcag gcactggtgg     2220
ttcccggctc tggcccggta aaagcccagg cggaagcgga aggtctggat aaaatcttta     2280
ttgaagccgg ttttgaatgg cgcttgcctg gctgctcaat gtgtctggcg atgaacaacg     2340
accgtctgaa tccgggcgaa cgttgtgcct ccaccagcaa ccgtaacttt gaaggccgcc     2400
aggggcgcgg cgggcgcacg catctggtca gcccggcaat ggctgccgct gctgctgtga     2460
ccggacattt cgccgacatt cgcaacatta ataaggagc acaccatggc agagaaattt     2520
atcaaacaca caggcctggt ggttccgctg gatgccgcca atgtcgatac cgatgcaatc     2580
atcccgaaac agttttttgca gaaagtgacc cgtacgggtt ttgcgcgcca tctgtttaac     2640
gactggcgtt ttctggatga aaaaggccaa cagccaaacc cggacttcgt gctgaacttc     2700
ccgcagtatc agggcgcttc cattttgctg gcacagaaaa acttcggctg tggctcttcg     2760
cgtgagcacg cgccctgggc attgaccgac tacggtttta aagtggtgat tgcgccgagt     2820
tttgctgaca tcttctacgg caatagcttt aacaaccagc tgctgccggt gaaattaagc     2880
gatgcagaag tggacgaact gtttgcgctg gtgaaagcta atcgggat ccatttcgac     2940 gtggatctgg aagcgcaaga ggtgaaagcg ggagagaaaa cctatcgctt taccatcgat     3000
```

```
gccttccgcc gccactgcat gatgaacggt ctggacagta ttgggcttac cttgcagcac    3060
gacgacgcca ttgccgctta tgaagcaaaa caacctgcgt ttatgaatta a             3111

<210> SEQ ID NO 7
<211> LENGTH: 497
<212> TYPE: DNA
<213> ORGANISM: Escherichia coli

<400> SEQUENCE: 7
gtgaaaccag taacgttata cgatgtcgca gagtatgccg gtgtctctta tcagaccgtt     60
tcccgcgtgg tgaaccaggc cagccacgtt tctgcgaaaa cgcgggaaaa agtggaagcg    120
gcgatggcgg agctgaatta cattcccaac cgcgtggcac aacaactggc gggcaaacag    180
tcgttgctga ttggcgttgc cacctccagt ctggccctgc acgcgccgtc gcaaattgtc    240
gcggcgatta aatctcgcgc cgatcaactg gtgccagcg tggtggtgtc gatggtagaa     300
cgaagcggcg tcgaagcctg taaagcggcg gtgcacaatc ttctcgcgca acgcgtcagt    360
gggctgatca ttaactatcc gctggatgac caggatgcca ttgctgtgga agctgcctgc    420
actaatgttc cggcgttatt tcttgatgtc tctgaccaga cacccatcaa cagtattatt    480
ttctcccatg aagacgg                                                   497

<210> SEQ ID NO 8
<211> LENGTH: 535
<212> TYPE: DNA
<213> ORGANISM: Escherichia coli

<400> SEQUENCE: 8
gctgttagcg ggcccattaa gttctgtctc ggcgcgtctg cgtctggctg gctggcataa     60
atatctcact cgcaatcaaa ttcagccgat agcggaacgg gaaggcgact ggagtgccat    120
gtccggtttt caacaaacca tgcaaatgct gaatgagggc atcgttccca ctgcgatgct    180
ggttgccaac gatcagatgg cgctgggcgc aatgcgcgcc attaccgagt ccgggctgcg    240
cgttggtgcg gatatctcgg tagtgggata cgacgatacc gaagacagct catgttatat    300
cccgccgtta accaccatca acaggatttt cgcctgctg gggcaaacca gcgtggaccg    360
cttgctgcaa ctctctcagg gccaggcggt gaagggcaat cagctgttgc ccgtctcact    420
ggtgaaaaga aaaaccaccc tggcgcccaa tacgcaaacc gcctctcccc gcgcgttggc    480
cgattcatta atgcagctgg cacgacaggt ttcccgactg gaaagcgggc agtga         535

<210> SEQ ID NO 9
<211> LENGTH: 897
<212> TYPE: DNA
<213> ORGANISM: Escherichia coli

<400> SEQUENCE: 9
atgaccatga ttacggattc actggccgtc gttttacaac gtcgtgactg ggaaaaccct     60
ggcgttaccc aacttaatcg ccttgcagca catccccctt cgccagctg gcgtaatagc     120 gaagaggccc gcaccgatcg cccttcccaa cagttgcgca gcctgaatgg cgaatggcgc    180
tttgcctggt ttccggcacc agaagcggtg ccggaaagct ggctggagtg cgatcttcct    240
gaggccgata ctgtcgtcgt cccctcaaac tggcagatgc acggttacga tgcgcccatc    300
tacaccaacg tgacctatcc cattacggtc aatccgccgt ttgttcccac ggagaatccg    360
acgggttgtt actcgctcac atttaatgtt gatgaaagct ggctacagga aggccagacg    420
```

```
cgaattatttt ttgatggcgt taactcggcg tttcatctgt ggtgcaacgg gcgctgggtc    480
ggttacggcc aggacagtcg tttgccgtct gaatttgacc tgagcgcatt tttacgcgcc    540
ggagaaaacc gcctcgcggt gatggtgctg cgctggagtg acggcagtta tctggaagat    600
caggatatgt ggcggatgag cggcattttc cgtgacgtct cgttgctgca taaaccgact    660
acacaaatca gcgatttcca tgttgccact cgctttaatg atgatttcag ccgcgctgta    720
ctggaggctg aagttcagat gtgcggcgag ttgcgtgact acctacgggt aacagtttct    780
ttatggcagg gtgaaacgca ggtcgccagc ggcaccgcgc ctttcggcgg tgaaattatc    840
gatgagcgtg gtggttatgc cgatcgcgtc acactacgtc tgaacgtcga aaacccg      897
```

```
<210> SEQ ID NO 10
<211> LENGTH: 500
<212> TYPE: DNA
<213> ORGANISM: Escherichia coli

<400> SEQUENCE: 10
ttgatggtag tggtcaaatg gcgattaccg ttgatgttga agtggcgagc gatacaccgc     60
atccggcgcg gattggcctg aactgccagc tggcgcaggt agcagagcgg gtaaactggc    120
tcggattagg gccgcaagaa aactatcccg accgccttac tgccgcctgt tttgaccgct    180
gggatctgcc attgtcagac atgtataccc cgtacgtctt cccgagcgaa acggtctgc    240 gctgcgggac gcgcgaattg aattatggcc acaccagtg gcgcggcgac ttccagttca    300
acatcagccg ctacagtcaa cagcaactga tggaaaccag ccatcgccat ctgctgcacg    360
cggaagaagg cacatggctg aatatcgacg gtttccatat ggggattggt ggcgacgact    420
cctggagccc gtcagtatcg gcggaattcc agctgagcgc cggtcgctac cattaccagt    480
tggtctggtg tcaaaaataa                                                500
```

```
<210> SEQ ID NO 11
<211> LENGTH: 22
<212> TYPE: DNA
<213> ORGANISM: Artificial Sequence
<220> FEATURE:
<223> OTHER INFORMATION: The sequence is synthesized.

<400> SEQUENCE: 11
gtgaaaccag taacgttata cg                                              22
```

```
<210> SEQ ID NO 12
<211> LENGTH: 52
<212> TYPE: DNA
<213> ORGANISM: Artificial Sequence
<220> FEATURE:
<223> OTHER INFORMATION: The sequence is synthesized.

<400> SEQUENCE: 12
ccacacatta tacgagccgg atgattaatt gtcaaccgtc ttcatgggag aa             52
```

```
<210> SEQ ID NO 13
<211> LENGTH: 80
<212> TYPE: DNA
<213> ORGANISM: Artificial Sequence
<220> FEATURE:
<223> OTHER INFORMATION: The sequence is synthesized.

<400> SEQUENCE: 13
ccggctcgta taatgtgtgg aattgtgagc ggataacaat ttcacacaag gagatatacc     60
atgtctccta acgatgcatt                                                 80
```

<210> SEQ ID NO 14
<211> LENGTH: 73
<212> TYPE: DNA
<213> ORGANISM: Artificial Sequence
<220> FEATURE:
<223> OTHER INFORMATION: The sequence is synthesized.

<400> SEQUENCE: 14
caaacaacag ataaaacgaa aggcccagtc tttcgactga gcctttcgtt ttatttgctt    60
aaacgccgcc agc    73

<210> SEQ ID NO 15
<211> LENGTH: 63
<212> TYPE: DNA
<213> ORGANISM: Artificial Sequence
<220> FEATURE:
<223> OTHER INFORMATION: The sequence is synthesized.

<400> SEQUENCE: 15
ttcgttttat ctgttgtttg tcggtgaacg ctctcctgag taggacaaat gctgttagcg    60
ggc    63

<210> SEQ ID NO 16
<211> LENGTH: 18
<212> TYPE: DNA
<213> ORGANISM: Artificial Sequence
<220> FEATURE:
<223> OTHER INFORMATION: The sequence is synthesized.

<400> SEQUENCE: 16
tcactgcccg ctttccag    18

<210> SEQ ID NO 17
<211> LENGTH: 20
<212> TYPE: DNA
<213> ORGANISM: Artificial Sequence
<220> FEATURE:
<223> OTHER INFORMATION: The sequence is synthesized.

<400> SEQUENCE: 17
atgtctccta acgatgcatt    20

<210> SEQ ID NO 18
<211> LENGTH: 15
<212> TYPE: DNA
<213> ORGANISM: Artificial Sequence
<220> FEATURE:
<223> OTHER INFORMATION: The sequence is synthesized.

<400> SEQUENCE: 18
ttaaacgccg ccagc    15

<210> SEQ ID NO 19
<211> LENGTH: 22
<212> TYPE: DNA
<213> ORGANISM: Artificial Sequence
<220> FEATURE:
<223> OTHER INFORMATION: The sequence is synthesized.

<400> SEQUENCE: 19
atgaccatga ttacggattc ac    22

<210> SEQ ID NO 20

```
<211> LENGTH: 58
<212> TYPE: DNA
<213> ORGANISM: Artificial Sequence
<220> FEATURE:
<223> OTHER INFORMATION: The sequence is synthesized.

<400> SEQUENCE: 20
ccacacatta tacgagccgg atgattaatt gtcaacgggt tttcgacgtt cagacgta      58

<210> SEQ ID NO 21
<211> LENGTH: 79
<212> TYPE: DNA
<213> ORGANISM: Artificial Sequence
<220> FEATURE:
<223> OTHER INFORMATION: The sequence is synthesized.

<400> SEQUENCE: 21
ccggctcgta taatgtgtgg aattgtgagc ggataacaat ttcacacaag gagatatacc    60
atgaatgtgg cagcttctc                                                 79

<210> SEQ ID NO 22
<211> LENGTH: 82
<212> TYPE: DNA
<213> ORGANISM: Artificial Sequence
<220> FEATURE:
<223> OTHER INFORMATION: The sequence is synthesized.

<400> SEQUENCE: 22
caaacaacag ataaaacgaa aggcccagtc tttcgactga gcctttcgtt ttatttgtta    60
gatcttggcc ggagccatgg tc                                             82

<210> SEQ ID NO 23
<211> LENGTH: 81
<212> TYPE: DNA
<213> ORGANISM: Artificial Sequence
<220> FEATURE:
<223> OTHER INFORMATION: The sequence is synthesized.

<400> SEQUENCE: 23
gactgggcct ttcgttttat ctgttgtttg tcggtgaacg ctctcctgag taggacaaat    60
ttgatggtag tggtcaaatg g                                              81

<210> SEQ ID NO 24
<211> LENGTH: 21
<212> TYPE: DNA
<213> ORGANISM: Artificial Sequence
<220> FEATURE:
<223> OTHER INFORMATION: The sequence is synthesized.

<400> SEQUENCE: 24
ttatttttga caccagacca a                                              21

<210> SEQ ID NO 25
<211> LENGTH: 49
<212> TYPE: DNA
<213> ORGANISM: Artificial Sequence
<220> FEATURE:
<223> OTHER INFORMATION: The sequence is synthesized.

<400> SEQUENCE: 25
atcatcacag cagcggcctg gtgccgcgca tgtctcctaa cgatgcatt                49

<210> SEQ ID NO 26
<211> LENGTH: 44
```

-continued

<212> TYPE: DNA
<213> ORGANISM: Artificial Sequence
<220> FEATURE:
<223> OTHER INFORMATION: The sequence is synthesized.

<400> SEQUENCE: 26
tgatgatgtt agctagcgct gaattctgct taaacgccgc cagc                44

<210> SEQ ID NO 27
<211> LENGTH: 52
<212> TYPE: DNA
<213> ORGANISM: Artificial Sequence
<220> FEATURE:
<223> OTHER INFORMATION: The sequence is synthesized.

<400> SEQUENCE: 27
gaccatggaa ttcgagctcg gtacccggat gtcgaagaat taccatattg cc        52

<210> SEQ ID NO 28
<211> LENGTH: 53
<212> TYPE: DNA
<213> ORGANISM: Artificial Sequence
<220> FEATURE:
<223> OTHER INFORMATION: The sequence is synthesized.

<400> SEQUENCE: 28
cttgcatgcc tgcaggtcga ctctagaata attcataaac gcaggttgtt ttg       53

<210> SEQ ID NO 29
<211> LENGTH: 53
<212> TYPE: DNA
<213> ORGANISM: Artificial Sequence
<220> FEATURE:
<223> OTHER INFORMATION: The sequence is synthesized.

<400> SEQUENCE: 29
agtcctaggt ataatactag tttctcccat gaagacgggt tttagagcta gaa       53

<210> SEQ ID NO 30
<211> LENGTH: 53
<212> TYPE: DNA
<213> ORGANISM: Artificial Sequence
<220> FEATURE:
<223> OTHER INFORMATION: The sequence is synthesized.

<400> SEQUENCE: 30
ttctagctct aaaacccgtc ttcatgggag aaactagtat tataccctagg act      53

<210> SEQ ID NO 31
<211> LENGTH: 58
<212> TYPE: DNA
<213> ORGANISM: Artificial Sequence
<220> FEATURE:
<223> OTHER INFORMATION: The sequence is synthesized.

<400> SEQUENCE: 31
agtcctaggt ataatactag taaactgtgg agcgccgaaa tccgttttag agctagaa  58

<210> SEQ ID NO 32
<211> LENGTH: 58
<212> TYPE: DNA
<213> ORGANISM: Artificial Sequence
<220> FEATURE:
<223> OTHER INFORMATION: The sequence is synthesized.

<400> SEQUENCE: 32

```
<210> SEQ ID NO 33
<211> LENGTH: 51
<212> TYPE: DNA
<213> ORGANISM: Artificial Sequence
<220> FEATURE:
<223> OTHER INFORMATION: The sequence is synthesized.

<400> SEQUENCE: 33
atcatcacag cagcggcctg gtgccgcgca tgaccatgat tacggattca c            51

<210> SEQ ID NO 34
<211> LENGTH: 52
<212> TYPE: DNA
<213> ORGANISM: Artificial Sequence
<220> FEATURE:
<223> OTHER INFORMATION: The sequence is synthesized.

<400> SEQUENCE: 34
tgatgatgtt agctagcgct gaattctgct tagatcttgg ccggagccat gg           52

<210> SEQ ID NO 35
<211> LENGTH: 22
<212> TYPE: DNA
<213> ORGANISM: Artificial Sequence
<220> FEATURE:
<223> OTHER INFORMATION: The sequence is synthesized.

<400> SEQUENCE: 35
atgaccatga ttacggattc ac                                            22

<210> SEQ ID NO 36
<211> LENGTH: 23
<212> TYPE: DNA
<213> ORGANISM: Artificial Sequence
<220> FEATURE:
<223> OTHER INFORMATION: The sequence is synthesized.

<400> SEQUENCE: 36
ttagatcttg gccggagcca tgg                                           23
```
ttctagctct aaaacggatt tcggcgctcc acagtttact agtattatac ctaggact      58